(12) United States Patent
Jacobsen et al.

(10) Patent No.: US 8,710,008 B2
(45) Date of Patent: Apr. 29, 2014

(54) COMPOUNDS, COMPOSITIONS AND USE

(75) Inventors: Oyvind Jacobsen, Oslo (NO); Jo Klaveness, Oslo (NO); Pal Rongved, Oslo (NO); Mahmood Amiry-Moghaddam, Oslo (NO); Ole Petter Ottersen, Oslo (NO)

(73) Assignee: Universitetet I Oslo, Oslo (NO)

( * ) Notice: Subject to any disclaimer, the term of this patent is extended or adjusted under 35 U.S.C. 154(b) by 0 days.

(21) Appl. No.: 13/141,465

(22) PCT Filed: Dec. 22, 2009

(86) PCT No.: PCT/GB2009/002942
§ 371 (c)(1),
(2), (4) Date: Oct. 11, 2011

(87) PCT Pub. No.: WO2010/073009
PCT Pub. Date: Jul. 1, 2010

(65) Prior Publication Data
US 2012/0245094 A1    Sep. 27, 2012

(30) Foreign Application Priority Data
Dec. 22, 2008   (GB) .................... 0823366.0

(51) Int. Cl.
*A61K 38/00*   (2006.01)
*C07K 14/00*   (2006.01)
*A61P 25/00*   (2006.01)
*A61K 38/16*   (2006.01)
*C07K 14/705*  (2006.01)

(52) U.S. Cl.
CPC ............. *A61K 38/00* (2013.01); *A61K 38/16* (2013.01); *C07K 14/00* (2013.01); *C07K 14/705* (2013.01)
USPC .......... 514/17.7; 530/329; 530/330; 514/21.3

(58) Field of Classification Search
CPC ....... A61K 38/00; A61K 38/16; C07K 14/00; C07K 14/705
See application file for complete search history.

(56) References Cited

U.S. PATENT DOCUMENTS
2007/0281978 A1   12/2007  Nakada et al.

FOREIGN PATENT DOCUMENTS

| WO | WO 2004/092207 | 10/2004 |
| WO | WO 2006/091734 | 8/2006 |
| WO | WO 2007/104062 | 9/2007 |
| WO | WO 2009/039854 | 4/2009 |
| WO | WO 2009/050498 | 4/2009 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitut~ons in Each Repeat, J. Mol. BIoL (2002) 324, 373-386.*
Muller, Prodrug Approaches for Enhancing the Bioavailability of Drugs eith Low Solubility, Chemistry & Biodiversity, 2009, 6, pp. 2071-2083.*
Beaumont, et, al, Design of Ester Prodrugs to Enhance Oral Absorption of Poorly Permeable Compounds: Challenges to the Discovery Scientist, Current Drug Metabolism, 2003, 4, 461-485.*
Hyo-Kyung Han, Targeted Prodrug Design to Optimize Drug Delivery, AAPS Pharmsci 2000; 2 (1) article 6 pp. 1-11.*
Yashveer Singh et al, Recent Trends in Targeted Anticancer Prodrug and Conjugate Design, Curr Med Chem. 2008 ; 15(18): 1802-1826.*
Testa B., Prodrug Research: Futile or Fertile?, Biochem. Pharm., 2004, 68, pp. 2097-2106.*
Ettmayer, P. et al, Lessons Learned from Marketed and Investigational Prodrugs,J. Med. Chem., 2004, 47 (10), pp. 2393-2404.*
Ohta et al, Amino Adds and Peptides. 1.1) Synthesis of a Model Peptide related to Iron-Sulfur Protein, Chem. Pharm. Bull., 1979, 27, pp. 2968-2974.*

(Continued)

*Primary Examiner* — Julie Ha
*Assistant Examiner* — Li Ni Komatsu
(74) *Attorney, Agent, or Firm* — Nixon & Vanderhye PC

(57) ABSTRACT

A peptide comprising a unit of formula (I) and having a molecular weight of less than 2000 wherein each X is independently an organic group, e.g. a $C_{1-6}$ alkyl or $C_{1-6}$ alkenyl group, preferably —$CH_2$—CH=$CH_2$, or the two X groups taken together can form a covalent or non-covalent link between the two O groups, preferably a $C_{1-10}$ saturated or unsaturated carbon chain optionally interrupted by one or more heteroatoms selected from O, S, N, P, or Si, especially a $C_{3-10}$ carbon chain or one X represents an azido group and the other an C2-6-alkynyl group; both Z's are the same and are O or S; each Y is independently C, CH, $CH_2$, N or NH; $R_1$ is H or $C_{1-6}$ alkyl; $R_2$ is H or $C_{1-6}$ alkyl; $R_5$ is a $C_{1-6}$ alkyl group, preferably isopropyl; or a salt, ester or prodrug thereof.

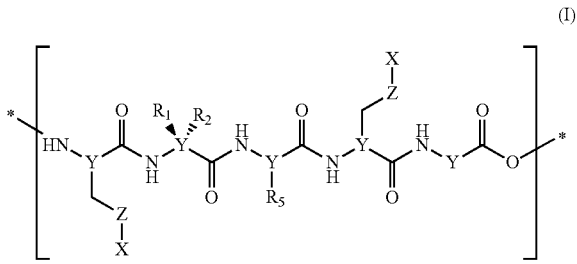

(I)

16 Claims, 1 Drawing Sheet

(56) References Cited

OTHER PUBLICATIONS

International Search Report for PCT/GB2009/002942, mailed Jul. 20, 2010.
Written Opinion of the International Searching Authority for PCT/GB2009/002942, mailed Jul. 20, 2010.
Jacobsen, O. et al., "Synthesis of Cyclic Peptide Analogues of the 3-10 Helical Pro138-Gly144 Segment of Human Aquaporin-4 by Olefin Metathesi", Organic & Biomolecular Chemistry, vol. 7, No. 8, (Apr. 21, 2009), pp. 1599-1611.
Tani, T. et al., "Identification of Binding Sites for Anti-Aquaporin 4 Antibodies in Patients with Neuromyelitis Optica", Journal of Neuroimmunology, vol. 211, (2009), pp. 110-113.
Sabater, L. et al., "Cytotoxic Effect of Neuromyelitis Optical Antibody (NMO-IgG) to Astrocytes: An in Vitro Study", Journal of Neuroimmunology, vol. 215, (2009), pp. 31-35.
Li, Y. et al., "Brian Magnetic Resonance Imaging Abnormalities in Neuromyelitis Optica", Acta Neurol Scand, vol. 118, (2008), pp. 218-225.
Lennon, V.A. et al., "IgG Marker of Optic-Spinal Multiple Sclerosis Binds to the Aquaporin-4 Water Channel", JEM, vol. 202, No. 4, (Aug. 15, 2005), pp. 473-477.
Nicchia, G.P. et al., "Aquaporin-4 Orthogonal Arrays of Particles are the Target for Neuromyelitis Optica Autoantibodies", GLIA 57, (2009), pp. 1363-1373.
Jacobsen, O. et al., "Synthesis of Cyclic Peptide Analogues of the 3-10 Helical Pro138-Gly144 Segment of Human Aquaporin-4 by Olefin Metathesi", Organic & Biomolecular Chemistry, vol. 7, No. 8, (Apr. 21, 2009), pp. 1599-1611.
R. Sogaard et al, Eur. J. Physiol, 456, 285-292 (2008).
B. Yang et al, FEBS Letters, 580, 6679-6684 (2006).
Y. Tanimura et al, J. Structural Biology, 166, 16-21 (2009).

* cited by examiner

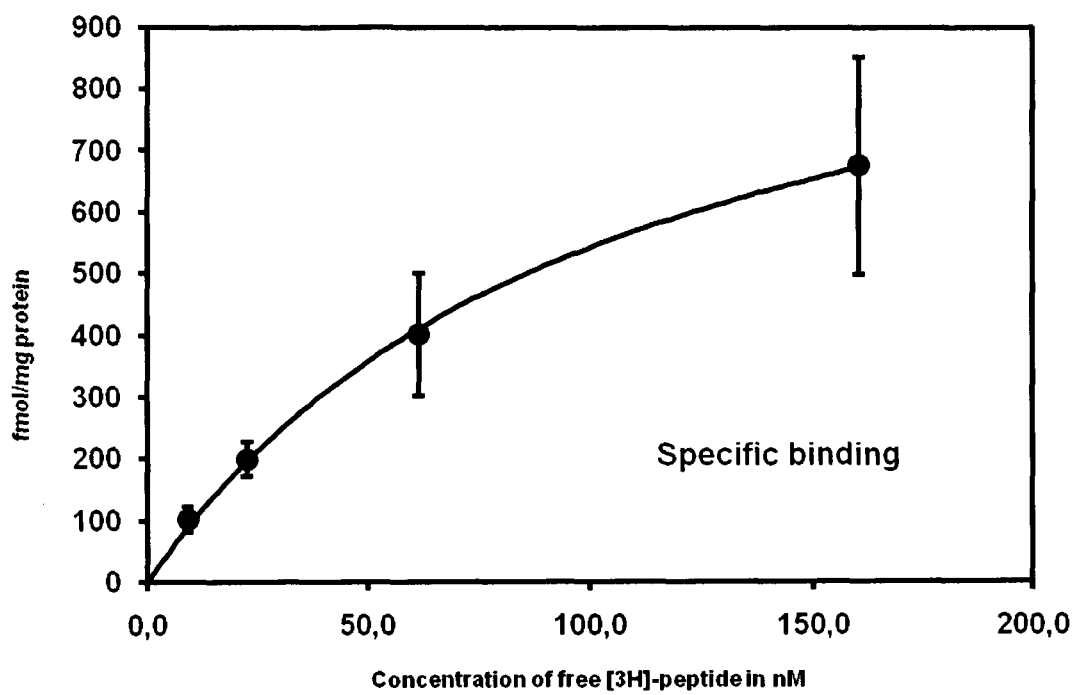

COMPOUNDS, COMPOSITIONS AND USE

This application is the U.S. national phase of International Application No. PCT/GB2009/002942, filed 22 Dec. 2009, which designated the U.S. and claims priority to GB Application No. 0823366.0, filed 22 Dec. 2008, the entire contents of each of which are hereby incorporated by reference.

This invention relates to compounds having specific aquaporin (hereinafter AQP) modulating activity, in particular compounds having a modulating activity on aquaporin 4 (AQP-4). In particular, the invention relates to compounds having no or negligible clinical effect on at least one of carbonic anhydrase, serotonin receptors, acetylcholine receptors, dopamine receptors, and in particular protein targets located in the central nervous system (CNS) when administered in doses suitable for treatment of aquaporin related diseases.

Aquaporins are intrinsic membrane channel proteins permeable to water and a few other small-molecular solutes. This class of proteins can be subdivided into the "pure" aquaporins (e.g. AQP4), which are only permeable to water, and the aquaglyceroporins (e.g. AQP3, AQP7 and AQP9), which, in addition to water, are also permeable to a few neutral solutes like glycerol, ammonia, short carbohydrates and urea. The aquaporins regulate the flow of water in and out cells. Ions and most other chemical components dissolved in the water do not pass through these channels. In particular, hydroxonium ions and other charged ions do not pass these water channels.

The aquaporins comprise six transmembrane alpha-helices arranged in a right-handed bundle with the terminal amino group and carboxylic group located on the cellular inside of the membrane.

There are thirteen types of aquaporins expressed in humans (AQP0-AQP12). These types of AQPs have different regulation and expression. The most described AQPs are aquaporin 1 (AQP 1), aquaporin 2 (AQP 2), aquaporin 3 (AQP 3) and aquaporin 4 (AQP 4). The location and function of these aquaporins is different. For example, AQP4 is mainly located in the skeletal muscle, kidneys and the central nervous system whereas AQP5 is present in the lungs and exocrine glands.

AQP1, located primarily in the kidneys and the capillaries (except capillaries of the CNS) might have a role related to various disease conditions like cyst formation in the kidneys, tumor growth, pulmonary edema and glaucoma.

AQP2 might have a role related to kidney diseases. Aquaglyceroporins might be related to diabetes and obesity.

AQP4 might be related to brain edema as a result of stroke, cancer, trauma, meningitis, and other brain related conditions such as epilepsy, Devic's disease (neuromyelitis optica), multiple sclerosis and Alzheimer's disease.

Although the existence and important functions of aquaporins have been known for many years, no drugs with modulating activity on aquaporins are in clinical use or in regulatory development. However, several known compounds and drugs are claimed to have a modulating activity on aquaporins.

Metal ions like mercury, silver and gold have been shown to inhibit most AQPs, with the exception of AQP4. This inhibition is reported to be through covalent modification of a cysteine residue, and is regarded as irreversible. Lead has been shown to increase the water permeability in a model expressing AQP4 and mercury chloride have been claimed to inhibit AQP4 in a liposome-based assay. The potential irreversible effects of these metal ions on the AQPs and the general toxicity of mercury and other metal ions exclude these salts as potential drug candidates for modulation of AQPs.

Tetraethylammonium salts and other quaternary ammonium salts are reported to inhibit AQP1, AQP2 and AQP4 with IC50 values in the micromolar range or higher. However, tetraethylammonium ions showed no effect in a recent study on AQP1 (R. Søgaard et al. in Eur. J. Physiol, 456, 285-292 (2008) nor on AQP4 (up to 10 mmolar concentration) (B. Yang et al. in FEBS Letters, 580, 6679-6684 (2006).

Moreover, quaternary ammonium salts have several disadvantages as potential drug candidates as they are permanently charged and will not be absorbed after oral administration. They also interact with other therapeutic targets.

Acetazolamide, which is a carbonic anhydrase inhibitor, has been reported to inhibit AQP1 mediated water permeability and inhibit AQP4 mediated water permeability but other studies disagree. In a recent study it was shown that azetazolamide reversibly inhibits water permeation through AQP4 but not through AQP1. The IC50 value was found to be higher than 1 mmolar (Y. Tanimura et al. in J. Structural Biology, 166, 16-21 (2009).

Other sulphonamide carbonic anhydrase inhibitors are claimed to have IC50 values down to 20 micromolar with regard to inhibition of AQP 1 and AQP4.

Various active drugs with different pharmacological mechanisms of action (including GABA-A receptor agonists, estrogen receptor antagonists, D2 receptor agonists, adrenergic beta receptor antagonists, 5HT1B/1D receptor agonists, antibiotics, bronchial expectorants) have recently been evaluated as potential AQP4 inhibitors both in vitro and in in silico docking studies.

In another recent study, various antiepileptic drugs have been tested as inhibitors of AQP4.

AQPs, especially AQP4, based on their pathophysiologically important roles in humans, are clinically important targets for new drugs. The drugs described in the prior art with potential modulating effects on AQPs including AQP4 are compounds with other pharmacological properties in addition to an alleged inhibitory effect on AQPs. In addition, these drugs also have several adverse effects. There is therefore a medical need for more specific AQP modulators, especially modulators and inhibitors that modulate or inhibit AQP4.

The inventors have found that certain peptides are able to modulate the activity of aquaporins. Ideally they should not interact with certain other receptors which could limit their clinical use.

SUMMARY OF THE INVENTION

Thus, viewed from one aspect the invention provides a peptide comprising a unit of formula (I)

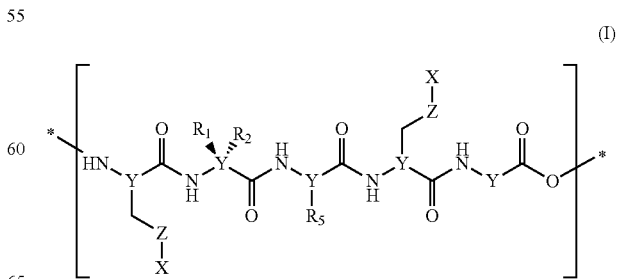

and having a molecular weight of less than 2000 preferably of formula (I')

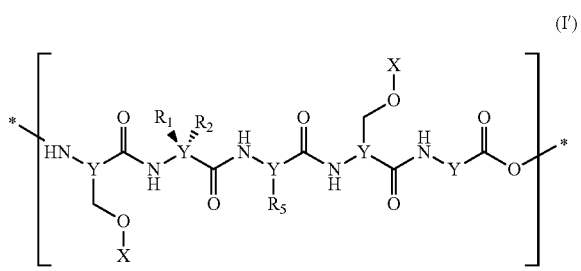

and having a molecular weight of less than 2000, more preferably of formula (I")

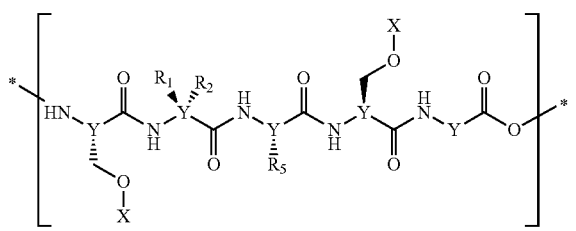

and having a molecular weight of less than 2000;

$R_1$ is H or $C_{1-6}$ alkyl;
$R_2$ is H or $C_{1-6}$ alkyl;
$R_5$ is a $C_{1-6}$ alkyl group, preferably isopropyl;
or a salt, ester or prodrug thereof.

Preferably compounds (I), (I') and (II') have groups $R_3$ and $R_4$ (defined in detail below) bound at the C and N termini (marked *) respectively.

Preferably the compound of the invention is of formula (II)

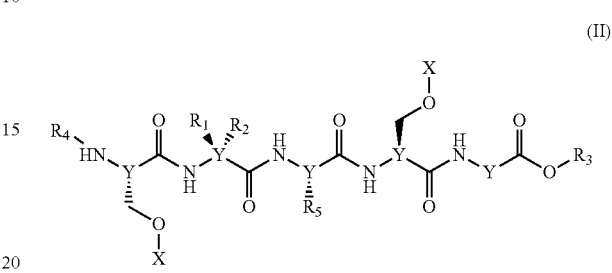

wherein $R_1$, $R_2$, $R_5$, X and Y are as hereinbefore defined; and $R_3$ and $R_4$ are protective groups for carboxylic groups or amino groups respectively, fluorescent probes, radiolabeled groups or a further peptide chain with 1-20 amino acids in the chain, the end groups of which may also carry protective groups for carboxylic groups or amino groups respectively, fluorescent probes, or radiolabeled groups.

In a highly preferred embodiment, the invention provides a compound of formula A or B:

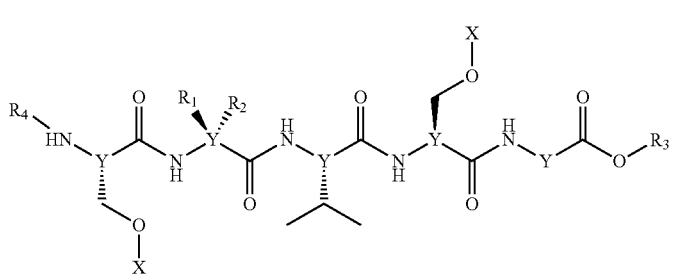

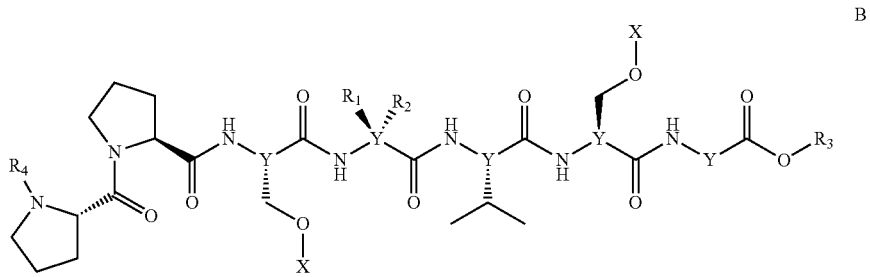

wherein each X is independently an organic group, e.g. a $C_{1-6}$ alkyl or $C_{1-6}$ alkenyl group, preferably —$CH_2$—CH=$CH_2$, or the two X groups taken together can form a covalent or non-covalent link between the two O groups, preferably a $C_{1-10}$ saturated or unsaturated carbon chain optionally interrupted by one or more heteroatoms selected from O, S, N, P, or Si, especially a $C_{3-10}$ carbon chain or one X represents an azido group and the other an $C_{2-6}$-alkynyl group;
both Z's are the same and are O or S;
each Y is independently C, CH, $CH_2$, N or NH;

wherein each X is independently an organic group, e.g. a $C_{1-6}$ alkyl or $C_{1-6}$ alkenyl group, preferably —$CH_2$—CH=$CH_2$, or wherein the two X groups taken together can form a covalent or non-covalent link between the two O groups, preferably a $C_{1-10}$ saturated or unsaturated carbon chain optionally interrupted by one or more heteroatoms selected from O, S, N, P, or Si, especially a $C_{3-10}$ carbon chain;
each Y is independently C or N, preferably C optionally comprising hydrogen to satisfy the valency of the atom;
each $R_1$ is independently $C_{1-6}$ alkyl or hydrogen;
each $R_2$ is independently $C_{1-6}$ alkyl or hydrogen; and R₃ and R₄ are protective groups for carboxylic groups or amino groups respectively, or activating groups, fluorescent probes, radiolabeled groups or peptide chains with 1-20 amino acids in the chain.

The present invention further relates to pharmaceutical compositions comprising a compound as herein before defined.

The invention also provides the use of a peptide as hereinbefore described in the treatment of disease, e.g. a disease associated with AQP.

The invention also provides a method of treating such a disease comprising administering to a patient in need thereof an effective amount of a peptide as hereinbefore defined.

In a still further aspect the invention provides use of an organic compound having a molecular weight of less than 2000 in the manufacture of a medicament for blocking interaction between AQPs and other in vivo proteins, or modulation of the function of AQPs, said AQP ligand having a binding affinity for an aquaporin, preferably aquaporin-4, having a dissociation constant of less than or equal to 10 micromolar, more preferably less than or equal to 1 micromolar, even more preferably less than or equal to 500 nanomolar, even more preferably less than or equal to 250 nanomolar, most preferably less than or equal to 200 nanomolar. Preferably modulation of the function of AQPs means inhibition of the function of AQPs. Preferably the AQP is AQP4.

Preferably the inhibitor has no or negligible effect on at least one of carbonic anhydrase, serotonin receptors, acetylcholine receptors, dopamine receptors for treatment of aquaporin related diseases.

BRIEF DESCRIPTION OF THE DRAWING

FIG. 1 shows the protein binding of radiolabeled compound 35 as a function of concentration.

DEFINITIONS

The compounds of the invention are ligands of AQPs, preferably modulators of AQPs, even more preferably inhibitors of AQP's. Ideally they have no other physiological effects. In particular, the compounds of the invention should have no effect or negligible effect on one or more of carbonic anhydrase, serotonin receptors, acetylcholine receptors or dopamine receptors.

By the term ligand of AQPs it is meant a compound having a binding affinity for an aquaporin, preferably aquaporin-4, having a dissociation constant of less than or equal to 10 micromolar.

By the term modulator of AQP's it is meant a compound having a binding affinity for an aquaporin, preferably aquaporin-4, having a dissociation constant of less than or equal to 10 micromolar, more preferably less than or equal to 1 micromolar, even more preferably less than or equal to 500 nanomolar, even more preferably less than or equal to 250 nanomolar, most preferably less than or equal to 200 nanomolar.

In addition, a modulator of an AQP should have the ability to either block the interaction of AQPs, particularly AQP4, with other in vivo proteins or change the function of the AQP as measured by its water permeability by more than 25%, more preferably by more than 50%, even more preferably by more than 75%, even more preferably by more than 90% at a concentration of less than 10 micromolar, more preferably less than 1 micromolar, even more preferably less than 500 nanomolar, even more preferably less 250 nanomolar, most preferably less than 200 nanomolar. By the term change the function of the AQP it is meant either increase or reduce the water permeability of the AQP.

By the term inhibitor of AQPs is meant a compound having a binding affinity for an aquaporin, preferably aquaporin-4, having a dissociation constant of less than or equal to 10 micromolar, more preferably less than or equal to 1 micromolar, even more preferably less than or equal to 500 nanomolar, even more preferably less than or equal to 250 nanomolar, most preferably less than or equal to 200 nanomolar.

In addition, inhibitors should also have the ability to either block the interaction of AQPs, particularly AQP4, with other in vivo proteins or reduce the function of the AQP as measured by its water permeability by more than 25%, more preferably by more than 50%, even more preferably by more than 75%, even more preferably by more than 90% at a concentration of less than 10 micromolar, more preferably less than 1 micromolar, even more preferably less than 500 nanomolar, even more preferably less 250 nanomolar, most preferably less than 200 nanomolar.

By the term no effect on one or more of carbonic anhydrase, serotonin receptors, acetylcholine receptors or dopamine receptors is meant that they do not change the natural response of these enzymes at all.

By negligible effect is meant that the inhibitory effect of the compound on other targets than AQPs is to reduce the function of the target by less than 25%, more preferably by less than 20%, even more preferably by less than 15%, even more preferably by less than 10%, even more preferably by less than 5%, even more preferably by less than 2%, most preferably by less than 1%.

DETAILED DESCRIPTION OF THE INVENTION

In any compound of the invention it is preferred if X is —$CH_2$—CH=$CH_2$. Alternatively, the two X groups taken together can form a bridge between the two serine residues in the peptide. That bridge may comprise 1 to 10 atoms in the backbone, preferably 3 to 8 atoms, especially 4 to 6 atoms, preferably 4 atoms. The number of bridging atoms will be counted between the two O groups of the serine residue in the peptide backbone.

It is preferred if the backbone atoms making up the bridge are all C atoms. More preferably, the bridge is an aliphatic chain, especially a saturated or unsaturated bridge. In the most preferred embodiment the linker is —$CH_2$CH=CH—$CH_2$— or —$CH_2CH_2CH_2CH_2$—.

In a further preferred embodiment one X represents an azido group and the other an acetylenic group.

Y is preferably C, CH, $CH_2$. It is especially preferred if the Y group reflects the structure of the amino acid used to form the peptide.

$R_1$ is preferably hydrogen or methyl, especially hydrogen.

$R_2$ is preferably $C_{1-6}$ alkyl such as methyl, isopropyl, —$CH_2$CH($Me_2$), or CH(Me)$CH_2CH_3$, especially isopropyl.

In a highly preferred embodiment $R_1$ and $R_2$ are methyl or $R_1$ is H when $R_2$ is isopropyl.

$R_5$ is preferably methyl, isopropyl, —$CH_2$CH($Me_2$), or CH(Me)$CH_2CH_3$, especially isopropyl.

Z is preferably O.

It will be appreciated therefore that the preferred backbone unit of any compound of the invention is based on a Ser-Val-Val-Ser-Gly backbone (SEQ ID NO: 1). It is preferred if any amino acid unit present is in the L form.

$R_3$ and $R_4$ are protective groups for carboxylic groups or amino groups respectively, or activating groups, fluorescent probes, radiolabeled groups or peptide chains with 1-20 amino acids in the chain. Preferably $R_3$ and $R_4$ are protective groups for carboxylic groups or amino groups respectively, or peptide chains with 1-20 amino acids in the chain.

It is especially preferred if $R_3$ is a protecting group for a carboxylic acid such as an ester, in particular a methyl ester or tert-butyl ester. Any standard C-terminus protecting group can however be used. C terminus protecting groups are well known in the art.

$R_4$ is preferably an amino protecting group such as Boc or carboxbenzyl (Z). Any known N terminus protecting group can be used here however and those are well known to the skilled man. Other examples include, Fmoc and alloc.

Alternatively, $R_4$ represents a further peptide chain, preferably containing 1 to 5 amino acid residues attached to the N terminus of the compound. In particular $R_4$ represents one or two additional amino acids (preferably essential amino acids), especially one or two additional proline residues attached to the N-terminus. It will be obvious to the skilled man that the N-terminus amino acid can then carry a N terminus protecting group such as Boc or Z or an activating group.

In a highly preferred embodiment therefore the peptides of the invention comprise 5 to 7 amino acids, especially 5 or 7 amino acids.

In a further highly preferred embodiment, the invention includes a Pro-Pro-Ser-Val-Val-Ser-Gly backbone (SEQ ID NO: 2).

In a highly preferred embodiment therefore the invention provides a compounds of formula Any compound of the invention will preferably have a Mw of less than 2000 D, preferably 300 D and 2000 D.

Peptides, Prodrugs & Peptidomimetics

Another aspect of the present invention is to use prodrugs to obtain selectivity for AQPs. The prodrugs of the present invention are compounds which may or may not bind to the AQP proteins, but are transformed in vivo to compounds with high affinity for AQP proteins. The rationale for AQP prodrugs is to improve selectivity, to reduce side effects and toxicity, to improve stability and/or to improve drug delivery of the active AQP interacting drug.

The invention also relates to peptidomimetics. These are compounds which have the same biological effects as the peptide but avoid some of the potential clinical disadvantages of a peptide. These disadvantages can typically be short shelf life, low oral bioavailability and low metabolic stability.

In particular peptidomimetics of the invention are those in which the backbone of the peptide is altered to be different from a conventional peptide, i.e. where Y is N for example, a peptidomimetic is formed.

The peptide AQP ligands according to the present invention are characterized by having a non-covalent interaction with the AQP proteins. This interaction preferably has a binding affinity for an aquaporin, preferably aquaporin-4, having a dissociation constant of less than or equal to 10 micromolar, more preferably less than or equal to 1 micromolar, even more preferably less than or equal to 500 nanomolar, even more

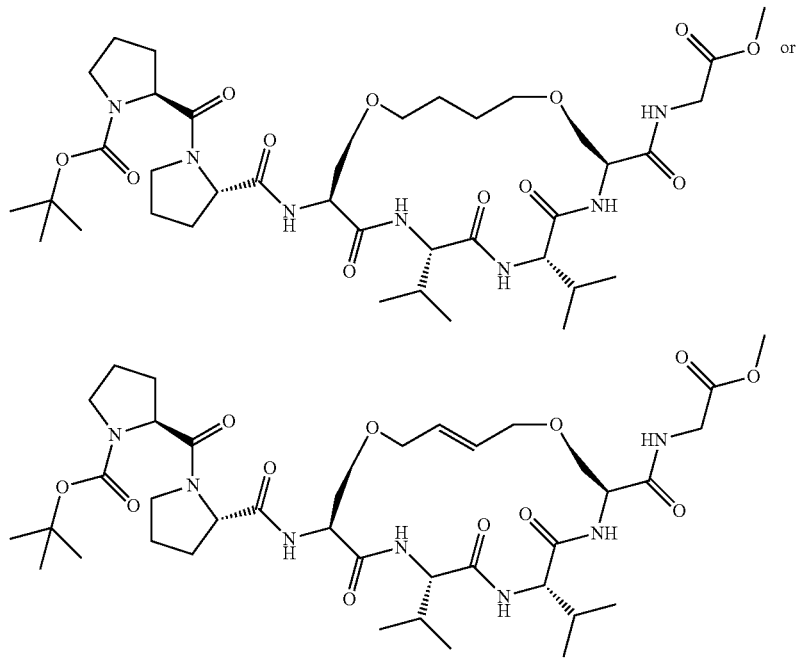

As noted above, $R_3$ and $R_4$ can be activating groups. In this regard, activating groups are those which might enhance the absorption of the compounds within the body or enhance efficacy.

One aspect of the present invention relates to CNS delivery of AQP4 inhibitors using prodrugs, especially lipophilic prodrugs of AQP inhibitors for example lipophilic esters or other bioreversible derivatives. A typical lipophilic prodrug for CNS delivery has preferably a log P value above 1.5, more preferably above 2.0.

preferably less than or equal to 250 nanomolar, most preferably less than or equal to 200 nanomolar.

The peptide AQP modulators of the present invention are reversible modulators of AQPs. It is believed that the peptides of the invention are able to mimic the extracelluar loop C of AQPs, in particular of AQP4 and AQP0.

In addition, the inventors have also found a further class of peptides, thought to interfere with anchoring of AQPs, in particular AQP4. In a second aspect, therefore the invention also provides a peptide compound of formula (III)

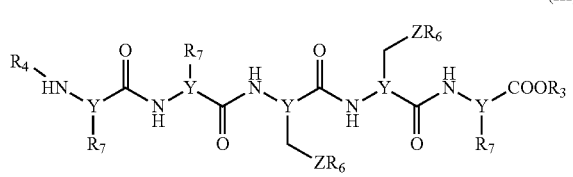

(III)

wherein Y, $R_3$, $R_4$ and Z are as hereinbefore defined;

$R_6$ is an acyl group comprising 2-16 C atoms, preferably a C2-6 acyl group such as an acetyl group; and $R_7$ is a $C_{1-6}$ alkyl, especially methyl, isopropyl, —$CH_2CH(Me_2)$, or $CH(Me)CH_2CH_3$.

Preferably the peptide is of formula (IV)

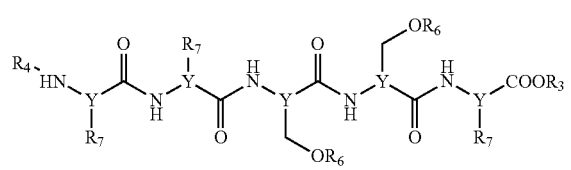

(IV)

More especially the peptide is of formula (V)

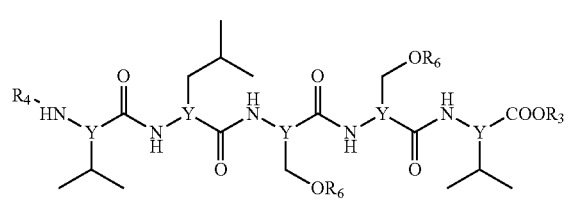

(V)

The preferred options for Y, Z, $R_3$ and $R_4$ above also apply to this embodiment. In particular, $R_3$ preferably represents a C terminal protecting group. $R_4$ preferably represents an additional amino acid chain having 1 to 7 units, preferably 2 to 5 units which in turn is preferably terminated with an N terminus protecting group.

Preferably the first amino acid attached to the N-terminus is Glu or Asp, especially Glu. If two amino acids are added, the second amino acid is preferably Gly. If three are added the third amino acid is preferably Ser or Cys. If four amino acids are added the 4th amino acid is also preferably Cys or Ser. A fifth amino acid is preferably Glu or Asp.

Additional units preferably form all of or part of the amino acid chain Asp-Ser-Ser-Gly-Glu (SEQ ID NO: 4), i.e. if one extra unit is added it is Glu, if two are added they are Gly and Glu etc. It is again stressed that the N-terminus amino acid should carry a protecting or activating group.

It is also preferred if any Glu or Asp group which is added can be functionalised to carry a C-terminus protecting group.

Most especially the invention provides a peptide of formula (VI)

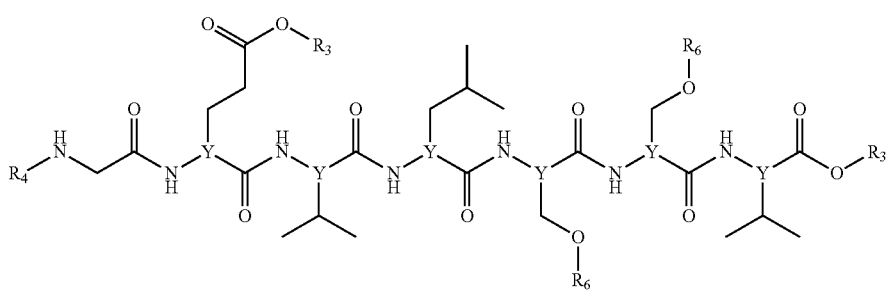

(VI)

in which the substituents are as hereinbefore defined.

Most especially peptides of this second embodiment will have the backbone structure Asp-Ser-Ser-Gly-Glu-Val-Leu-Ser-Ser-Val (SEQ ID NO: 3) in which the two serine residues nearest the C terminus carry the $R_6$ groups and the Glu residue carries an $R_3$. The serine residues towards the N-terminus can be in their native form or carry an $R_6$ group. The Asp residue may also carry an $R_3$.

It will again be appreciated that the N terminus of the formed amino acid should have a suitable protecting group or activating group thereon. Such groups are comprehensively described above.

It is believed that the peptides of this second aspect can pass the blood brain barrier and inhibit AqP4 activity through antagonism of the AqP4-PDZ domain on α-Synthropin and fits into our patent strategy in the peptide part of our patent application.

Synthesis

The peptides can be prepared using standard methods of peptide synthesis including both solid phase, solution phase chemistry and a combination of solution phase and solid phase chemistry. We exemplify the preparation of many peptides in the examples and the general procedures in these examples enable the formation of the claimed materials.

The synthesis of a bridge is shown in Scheme I

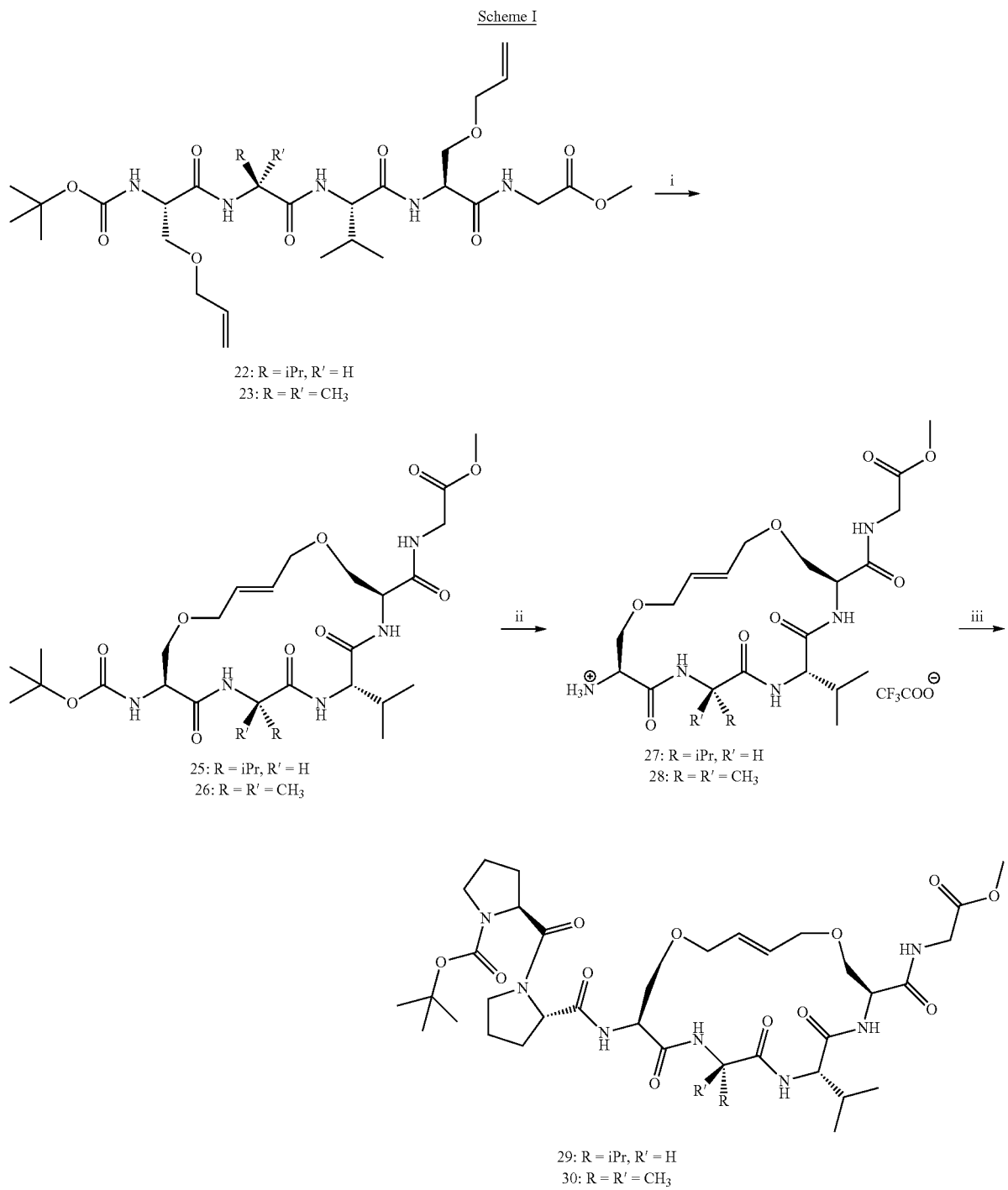

Synthesis of 29: (i) Grubbs' 2nd generation catalyst (20 mol %), DCM, rt, 7 h 30 min, 42%; (ii) TFA, DCM, rt, 1 h 50 min, 95%; (iii) Boc-Pro-Pro-OH, EDC, HOBt, DIPEA, DCM, 0° C. to rt, 21 h 30 min, 78%; OR Synthesis of 30: (i) Grubbs' 2nd generation catalyst (15 mol %), DCM, rt, 4 h 15 min, 52%; (ii) TFA, DCM, rt, 2 h, 71%; (iii) Boc-Pro-Pro-OH, EDC, HOBt, DIPEA, DCM, 0° C. to rt, 82%

Synthesis of a saturated bridging linker can be achieved easily by hydrogenation of the unsaturated linker such as that depicted above.

Dosages

The effective dose for treatment of a condition related to AQPs will be readily determined by the skilled man. Ideally it should be a dose resulting in unacceptable side effects for less than 1 out of 100 patients.

The IC50 value for modification of other pharmacological or toxicological targets should preferably be at least 100% higher than the IC50 value for modification of AQPs, more preferably at least 200% higher especially at least 300% higher, such as at least 400% higher than the IC50 value for modification of AQPs. Even more preferably, the IC50 value for modification of other pharmacological or toxicological targets should preferably be at least 500% higher than the IC50 value for modification of AQPs. Most preferably, the IC50 value for modification of other pharmacological or toxicological targets should preferably be at least 1000% higher than the IC50 value for modification of AQPs.

Preferably IC50 values are lower than 1 millimol per kilogram bodyweight.

Other Compounds

All organic AQP modulators described in the prior art are known drugs or compounds with known biological effects.

AQP modulators according to the present invention can be used in a neutral form or in the form of a pharmaceutically acceptable salt. Anionic AQP modulators are according to the present invention preferably used as salts with pharmaceutically acceptable ions like for example sodium, calcium, magnesium, meglumine, ammonium, aluminium, zinc, piperazine, tromethamine, lithium, choline, diethylamine, 4-phenylcyclohexylamine and benzathine. Cationic AQP modulators are according to the present invention preferably used as salts with pharmaceutically acceptable ions like for example chloride, sulphate, bromide, tartrate, oxalate, mesylate, maleate, citrate, phosphate, acetate, pamoate, iodide, nitrate, lactate, tosylate and besilate.

The AQP modulators according to the present invention may be characterized by having a non-covalent interaction with the AQP proteins. This interaction has preferably a dissociation constant lower than 10 micromolar, more preferably a dissociation constant lower than 1 micromolar, more preferably a dissociation constant lower than 500 nanomolar, even more preferably a dissociation constant lower than 250 nanomolar, most preferably a dissociation constant lower than 200 nanomolar.

Compositions

Viewed from a further aspect the invention provides a pharmaceutical composition comprising an AQP ligand, more preferably an AQP modulator, even more preferably an AQP inhibitor (in particular an AQP4 ligand, modulator or inhibitor), ester, prodrug or salt thereof according to the invention together with at least one physiologically tolerable carrier or excipient.

Another preferred aspect the invention provides a pharmaceutical composition comprising a selective AQP4 modulator or inhibitor or prodrug or salt thereof according to the invention together with at least one physiologically tolerable carrier or excipient for treatment of disorders in the central nervous system.

Preferably said modulator binds non-covalently to AQP4 in the central nervous system.

The carriers or excipients used in the compositions may be any of the material commonly used in pharmaceutical compositions, e.g. solvents (for example water), pH modifiers, viscosity modifiers, fillers, diluents, binders, aromas, skin penetration enhancers, antioxidants and other preservatives, etc. The choice will depend on the dosage administration route and form. Typically parenteral compositions, especially injectable compositions will be sterile.

The compositions of the invention may be in any convenient dosage administration form, e.g. solutions, dispersions, suspensions, syrups, tablets, coated tablets, powders, sprays, suppositories, etc. Solutions, dispersions, capsules and tablets are preferred, especially tablets, capsules and solutions for injection.

Tablets comprising AQP modulators according to the present invention can be prepared by direct compression, wet granulation, dry granulation or fluid bed granulation. Tablets, according to the present invention, will in addition to AQP modulating substance(s) and optionally other active pharmaceutical ingredients always comprise one or more well known tablet exipients. Such tablet excipients include typically antiadherents like magnesium stearate, binders like carbohydrates as starch, cellulose, microcrystalline cellulose, hydroxypropyl cellulose, lactose, microcrystalline cellulose, sugar alcohols like xylitol, sorbitol or manitol, polyethylene glycol, polyvinylpyrrolidone and gelatine, disintegrants like crosslinked polyvinyl pyrrolidone, sodium starch glycolate and sodium carboxymethyl cellulose, diluents and fillers like cellulose and dibasic calcium phosphate, flavors like mint, cherry vanilla, peach and apricot extracts, colours, glidants like silicon dioxide, talc and magnesium carbonate. Tablets are preferably coated with a film coating. Typical film coating materials to be used for film coated tablets according to the present invention include hydroxypropyl methyl cellulose (HPMC). Tablets might also be coated with en enteric coating. Typical enteric coating materials to be used for enteric coated tablets according to the present invention are various acrylate based polymers like Eudragit® and cellulose acetate phthalate (CAP).

Capsules are, according to the present invention, preferably hard gelatine capsules. The capsules might in addition to AQP modulating substance(s) and optionally other pharmaceutically active ingredients comprise of lactose and other additives.

Ready for use solutions comprising AQP modulators according to the present invention have preferably an osmolality in the same range as osmalality in blood. The solutions are preferably isotonic with blood (osmolality of appr. 300 mOsm/kg). Hypertonic solutions might also be acceptable in the administration volume is low (less than 10 ml). Solutions for injection or infusion are sterile. The pH value for injection or infusions is preferably within range 2 to 8, more preferably between 4 and 7.4. These formulations may be prepared in conventional fashion.

The administration route for the compounds and compositions of the invention may be enteral, e.g. oral, rectal or by tube, nasal, sub-lingual, by injection or infusion, e.g. i.v, i.p., i.m. or s.c. or, less preferably epidural or intracerebroventricular.

The daily dose of AQP modulator according to the present invention varies over a large range; depending upon medical condition and indication, severity, age and sex. A typical dose is between 0.1 mg to 3 gram daily, more preferably 0.2 mg to 2 grams daily, even more preferably 0.3 mg to 1.5 grams daily, most preferred 0.5 mg to 1 gram daily.

The composition of AQP modulator might, according to the present invention be administered once or several times for treatment of the medical condition. If the AQP modulator is administered several times for treatment of the same medical condition, the AQP modulator might be administered once monthly, once weekly or more frequently. The AQP modulator might be administered once daily or up to 6 times during 24 hours.

The dose of AQP modulator in one single unit dose may vary. Tablets and capsules might comprise from 0.1 mg to 1 gram per single dose unit, while solutions of AQP modulators might comprise of 0.1 mg to 3 grams of AQP modulator in one single dose.

The AQP inhibitors might, according to the present invention, be administered together with one or more other drug that do not modify AQP. The other drug(s) might be formulated in the same single dose unit (e.g tablet, capsule, solution) as the AQP modulator or might be formulated separately. If AQP modulator is used together with other drugs that do not modify AQP, the non-AQP modulating drug might be administered prior to the AQP modulating drug, together with the AQP modulating drug or after administration of the AQP modulating drug.

Typical non-AQP modulating drugs to be administered together with AQP modulating drugs are dependent on indication and the medical condition. This includes for example drugs with affinity for acetylcholine receptors (including both nicotinic receptors and muscarinic receptors, agonists like for example pilocarpine, antagonists like tropane derivatives), drugs with affinity for adrenergic receptors (like for example agonists like adrenaline, beta-2 antagonists like propranolol, beta2-agonists like salbutamol, beta-agonists like isoprenaline, alpha-2 agonists like methyldopa, and alpha-1 antagonists like ergotamine and alpha agonists like xylometazoline), drugs with affinity for GABA receptors (including barbiturates, agonists like benzodiazepines and antagonists like flumazenil), drugs with affinity for glutamate (NMDA) receptors (including antagonists like memantine and modulators like acamprostate), drugs with affinity for angiotensin receptors (including AT1 antagonists like losartan), drugs with affinity for dopamine receptors (including agonists like dopamine and antagonists like chlorpromazine), drugs with affinity for endothelin receptors (including antagonists like bosentan), drugs with affinity for histamine receptors (including H1 antagonists like diphenhydramine and H2 antagonists like ranitidine), drugs with affinity for cannabinoid receptors (including agonists like dronabinol), drugs with affinity for opioid receptors (including agonists like morphine and antagonists like buprenorphine), drugs with affinity for serotonin receptors (including all subgroups and including agonists like triptans and antagonists like quetiapine, drugs with affinity for cytokine receptors, drugs with affinity for integrin receptors, drugs with affinity for nuclear receptors, drugs that interact with ion channels like calcium channels, sodium channels, potassium channels and chloride channels, drugs that inhibit enzymes like redox enzymes, transferases, hydrolases, isomerases, lysases, ligases, drugs that interact with transport proteins, drugs with affinity for nucleic acids and ribosomes, monoclonal antibodies and drugs that modify various physicochemical mechanisms in the body.

Viewed from a further aspect the invention provides an AQP ligand, modulator or inhibitor or prodrug or salt thereof according to the invention for medical use.

Viewed from a still further aspect the invention provides the use of a AQP ligand, modulator or inhibitor or prodrug or salt thereof according to the invention for the manufacture of a medicament for use in treating a condition associated with AQP, e.g. a condition of the central nervous system.

Viewed from a yet still further aspect the invention provides a method of treatment of a human which method comprises administering a AQP ligand, modulator or inhibitor to the human subject. One preferred aspect of this method is administration of AQP4 modulators or inhibitors.

Indications

The conditions treated according to the invention will generally be conditions responsive to AQP ligands, modulators or inhibitors. Some of these indications are: disease conditions in the central nervous system preferably edema, stroke, cancer, Alzheimer's disease, schizophrenia, depression and various psychosis, various diseases related to the urogenital system including the kidneys, conditions related to the reproductive system, Meniere's disease, Sjøgren's Syndrome, skin conditions including cosmetics and skin diseases, wound healing, obestity, eye diseases, neuromyelitis optica, various infections and cancer.

The most preferred conditions to be treated are conditions responsive to AQP4 ligands, modulators or inhibitors. Such conditions may be associated for example with disease conditions in the central nervous system preferably edema, stroke, cancer, Alzheimer's disease, schizophrenia, depression and various psychosis. The even most preferred conditions for AQP4 inhibitors are brain edema and stroke.

The invention also encompasses the use of the compounds of the invention for treatment of demyelinating diseases like multiple sclerosis (MS) and multiple sclerosis borderline diseases, such as optic-spinal MS, acute disseminated encephalomyelitis, balo concentric sclerosis, Schilder disease, Marburg multiple sclerosis and Devic's disease, also known as Devic's syndrome or neuromyelitis optica (NMO).

A preferred aspect of the invention is use of the said compounds in treatment of NMO. NMO is an MS-like autoimmune, inflammatory disease in which the immune defense attacks the spinal cord and optic nerves. There is currently no cure for NMO. Typically, NMO has a worse outcome than MS, with frequent and early relapses. Vision and ambulation are impaired within 5 yrs of its onset in 50% of patients, and 20% succumb to respiratory failure from cervical myelitis.

Many clinicians agree that long term immunosuppression is required to reduce the frequency and severity of attacks, while others argue the exact opposite. Commonly used immunosuppressant treatments include azathioprine (Imuran) plus prednisone, mycophenolate mofetil plus prednisone, Rituximab, Mitoxantrone, intravenous immunoglobulin (IVIG), and Cyclophosphamide. The monoclonal antibody rituximab is under study. In 2007, Devic's disease was reported to be responsive to glatiramer acetate and to low-dose corticosteroids.

The target of the autoimmune attack has been identified to be aquaporin-4 (AQP4), in particular AQP4 orthogonal arrays. The attack is believed to be mediated by antibodies known as NMO-IgG, which bind to the extracellular surface of the protein, partly by recognition of loop C. Binding of the said compounds to AQP4 prevents binding of NMO-IgG to AQP4 and thus prevents or inhibits an autoimmune attack with subsequent demyelination.

Another preferred aspect of the invention is use of the said compounds in treatment of single or recurrent events of longitudinally extensive myelitis, bilateral simultaneous or recurrent optic neuritis, Asian optic-spinal MS, longitudinally extensive myelitis or optic neuritis associated with systemic autoimmune disease and optic neuritis or myelitis associated with lesions in specific brain areas such as the hypothalamus, periventricular nucleus, and brainstem. Patients with these conditions have generally NMO-IgG seropositive status.

This aspect of the invention, i.e. use of the said compounds in treatment of the said conditions, is completely separate from the use of the said compounds as AQP4 inhibitors against brain edema and the compounds used for this aspect of the invention need not have any effect on the water permeability of AQP4. The only property required is binding affinity towards the extracellular part of AQP4.

The invention is illustrated further by the following non-limiting Examples and FIGURE. FIG. 1 shows the protein binding of radiolabelled compound 35 as a function of concentration.

EXAMPLE 1

N-tert-butoxycarbonyl L-prolyl L-proline methyl ester (1)

METHOD 1 N-tert-butoxycarbonyl L-proline (99.69 g, 0.4631 mol) was dissolved in $CH_2Cl_2$ (800 mL). The solution was cooled to 0° C. (icebath) and triethylamine (51.50 g, 0.5089 mol) added. Pivaloyl chloride (61.45 g, 0.5096 mol) was added dropwise, resulting in the precipitation of a white solid. The reaction mixture was stirred for 1 hour at 0° C. before triethylamine (102.99 g, 1.018 mol) was added. Next, L-proline methyl ester hydrochloride (76.87 g, 0.4641 mol) was added in small portions. The icebath was removed and the reaction mixture stirred at room temperature for 17 hours. The volume was increased by addition of $CH_2Cl_2$ (2 L) and the solution washed with 30% (w/w) aqueous citric acid (3×1400 mL), saturated $NaHCO_3$ solution (3×1400 mL) and saturated brine (2×1400 mL). The solution was dried with anhydrous $MgSO_4$ and the solvent evaporated affording the title compound as a clear oil (129.14 g, 85%) with spectral characteristics in accordance with literature data.[1]

METHOD 2 N-tert-butoxycarbonyl L-proline (3.04 g, 14.1 mmol) and L-proline methyl ester hydrochloride (2.34 g, 14.1 mmol) were dissolved in $CH_2Cl_2$ (25 mL). N,N-diisopropylethylamine (1.82 g, 14.1 mmol) was added and the solution cooled to 0° C. (icebath). HOBt hydrate (2.16 g, 14.1 mmol) and then EDC hydrochloride (2.97 g, 15.5 mmol) were added together with 15 mL $CH_2Cl_2$. The icebath was removed and the reaction mixture stirred for 16 h 15 min at room temperature. The reaction mixture was diluted with $CH_2Cl_2$ (60 mL) and the solution washed with 1M HCl(3×25 mL), 7.5% (w/w) $K_2CO_3$ solution (3×25 mL) and saturated brine (25 mL). The solution was dried with anhydrous $MgSO_4$ and the solvent evaporated affording the title compound as a very pale yellow, almost clear oil, which was dried under high vacuum overnight. The compound (3.67 g, 79%) showed spectral characteristics in accordance with published data[1]; $\delta_H$ (200 MHz; $d_6$-DMSO) 4.56-4.31 (2H, m, $C^\alpha H(Pro_1)/C^\alpha H(Pro_2)$), 3.78-3.28 (4H, m, $C^\delta H_2(Pro_1)/C^\delta H_2(Pro_2)$), 3.67 (3H, s, $OCH_3$, rotomer 1), 3.65 (3H, s, $OCH_3$, rotomer 2), 2.26-1.65 (8H, m, $CH_2$), 1.40/1.34/1.22 (9H, s, $(CH_3)_3$, all rotomers); $\delta_C$ (75 MHz; $CDCl_3$) 172.8, 172.5, 171.5, 171.0, 154.4, 153.6, 79.3, 58.5, 57.6, 57.5, 53.3, 52.0, 51.9, 46.7, 46.5, 46.3, 29.8, 28.9, 28.7, 28.6, 28.3, 28.2, 24.9, 24.8, 23.9, 23.4

EXAMPLE 2

N-tert-butoxycarbonyl L-prolyl L-proline (2)

N-tert-butoxycarbonyl L-prolyl L-proline methyl ester 1 (1.10 g, 3.37 mmol) was dissolved in THF (23 mL) and the solution cooled to 0° C. (icebath). LiOH monohydrate (0.156 g, 3.72 mmol) was dissolved in de-ionized $H_2O$ (11.5 mL) and the solution cooled to 0° C. before being added dropwise to the solution of 1 over 5 min. The icebath was removed and stirring continued for an additional 3 h 30 min before solid $NaHCO_3$ (0.566 g, 6.74 mmol) was added. Stirring was continued for 20 minutes and the THF evaporated. The solution was diluted with $H_2O$ (11.5 mL), washed with $Et_2O$ (2×11.5 mL) and acidified to pH 2 by addition of 2M aqueous $H_2SO_4$. The resulting solution was extracted with $CH_2Cl_2$ (70 mL+4× 23 mL). The combined organic extracts were dried with anhydrous $MgSO_4$ and the solvent evaporated affording the title compound as a white solid (0.933 g, 89%) with spectral characteristics in accordance with literature data[1]; $\delta_H$(300 MHz; $d_6$-DMSO) 12.41 (1H, br s, COOH), 4.45-4.21 (2H, m, $C^\alpha H(Pro_1)/C^\alpha H(Pro_2)$), 3.73-3.13 (4H, m, $C^\delta H_2(Pro_1)/C^\delta H_2(Pro_2)$), 2.29-1.61 (8H, m, $CH_2$), 1.37/1.30/1.16 (9H, s, $(CH_3)_3$, all rotomers); $\delta_C$ (75 MHz; $CDCl_3$) 173.8, 173.5, 173.3, 173.0, 154.6, 153.6, 79.9, 59.6, 59.5, 57.7, 57.6, 47.1, 47.0, 46.9, 46.7, 30.0, 29.2, 28.4, 28.3, 27.7, 27.5, 25.0, 24.2, 23.6; m/z (ESI) 335.1595 ($[M+Na]^+$; $C_{15}H_{24}N_2O_5Na$ requires 335.1582)

EXAMPLE 3

N-tert-butoxycarbonyl O-allyl L-serine (3)

N-tert-butoxycarbonyl L-serine (27.04 g, 0.1318 mol) was dissolved in DMF (220 mL). The solution was cooled to 0° C. (icebath) before sodium hydride (60% dispersion in mineral oil, 11.59 g, 0.2898 mol) was added slowly under stirring. After gas evolution had ceased allyl bromide (17.54 g, 0.1450 mol) was added dropwise and the reaction mixture stirred for 18 hours at room temperature. The solvent was evaporated and the residue dissolved in $H_2O$ (500 mL). The solution was washed with $Et_2O$ (2×250 mL), cooled to 0° C. (icebath) and acidified to pH 2.5 by addition of 2M aqueous $H_2SO_4$. The resulting solution/suspension was extracted with EtOAc (5×250 mL). The combined organic extracts were dried with anhydrous $MgSO_4$ and the solvent evaporated overnight affording the title compound as a slightly yellow-orange viscous liquid (26.86 g, 83%) with spectral characteristics in accordance with published data;[3,4] $\delta_H$ (200 MHz; $d_6$-DMSO) 12.52 (1H, br s, COOH), 6.84 (1H, d, J 8, NH), 5.81 (1H, ddt, J 5, 10 and 17, $CH=CH_2$), 5.20 (1H, ddd, J 1, 3 and 17, $CH=CHH$), 5.09 (1H, ddd, J 1, 3 and 10, $CH=CHH$), 4.10 (1H, dt, J 5 and 8, $C^\alpha H$), 3.96-3.92 (2H, dt, J 1 and 5, $CH_2CH=CH_2$), 3.56 (2H, d, J 5, $CH_2$), 1.34 (9H, s, $(CH_3)_3$); $\delta_C$ (75 MHz; $d_6$-DMSO) 171.9, 155.3, 134.8, 116.5, 78.1, 71.0, 69.1, 53.7, 28.1; m/z (ESI) 268.0 ($[M+Na]^+$)

EXAMPLE 4

N-tert-butoxycarbonyl L-valyl L-valine methyl ester (4)

N-tert-butoxycarbonyl L-valine (28.36 g, 0.1305 mol) was dissolved in DMF (120 mL) and the solution cooled to 0° C. (icebath). L-valine methyl ester hydrochloride (21.88 g, 0.1305 mol) was suspended in DMF (60 mL) and N,N-diisopropylethylamine (16.87 g, 0.1305 mol) added. The resulting suspension was added to the solution of N-tert-butoxycarbonyl L-valine in one portion. HOBt hydrate (19.99 g, 0.1305 mol) and EDC hydrochloride (27.52 g, 0.1436 mol) were added together with additional DMF (80 mL). After 1 hour the icebath was removed and the reaction mixture stirred for 20 hours. The solvent was evaporated and the residue taken up in EtOAc (600 mL) and washed with 2 M aqueous $H_2SO_4$ (3×250 mL), 7.5% (w/w) aqueous $K_2CO_3$ (3×250 mL) and saturated brine (200 mL). The solution was dried with anhydrous $MgSO_4$ and the solvent evaporated affording the title compound as a white solid (37.50 g, 87%) with spectral characteristics in accordance with literature data[2]; $\delta_H$ (200 MHz; $d_6$-DMSO) 7.97 (1H, d, J 8, $NH(Val_2)$), 6.68 (1H, d, J 9, $NH(Val_1)$), 4.18 (1H, dd, J 6 and 9, $C^\alpha H(Val_1)$), 3.86 (1H, dd, J 8 and 8, $C^\alpha H(Val_2)$); 3.61 (3H, s, $OCH_3$), 2.12-1.83 (2H, m, $CH(CH_3)_3$), 1.37 (9H, s, $(CH_3)_3$), 0.91-0.80 (12H, m, $CH_3$); $\delta_C$ (50 MHz; $d_6$-DMSO) 171.7, 171.7, 155.3, 77.9, 59.4, 57.2, 51.5, 30.2, 29.8, 28.0, 19.0, 18.8, 18.1, 18.1; m/z (ESI) 353.2 ($[M+Na]^+$)

EXAMPLE 5

N-tert-butoxycarbonyl α,α'-dimethylglycyl L-valine methyl ester (5)

N-tert-butoxycarbonyl α,α-dimethylglycine (25.10 g, 0.1235 mol) was dissolved in DMF (150 mL). L-valine methyl ester hydrochloride (20.70 g, 0.1235 mol) and N,N-diisopropylethyl amine (15.96 g, 0.1235 mol) were dissolved in DMF (30 mL) and added. HOBt hydrate (18.91 g, 0.1235 mol) and EDC hydrochloride (26.05 g, 0.1359 mol) were added together with additional DMF (70 mL). The reaction mixture was stirred for 47 hours before the solvent was evaporated and the residue taken up in EtOAc (600 mL). The solution was washed with 2 M aqueous $H_2SO_4$ (3×250 mL), 7.5% (w/w) aqueous $K_2CO_3$ (3×250 mL) and saturated brine (250 mL). The solution was dried with anhydrous $MgSO_4$ and the solvent evaporated affording the title compound as a white solid (37.07 g, 95%) with spectral characteristics in accordance with literature data[7]; $\delta_H$ (200 MHz; $d_6$-DMSO) 7.38 (1H, d, J 8, NH(Val)), 6.93 (1H, br s, NH(Aib)), 4.21-4.14 (1H, m, $C^\alpha H$(Val)), 3.63 (3H, s, $OCH_3$), 2.13-1.97 (1H, m, $CH(CH_3)_2$), 1.37 (9H, s, $(CH_3)_3$), 1.32 (3H, s, $CH_3$(Aib)), 1.29 (3H, s, $CH_3$(Aib)), 0.85 (3H, d, J 7, $CH_3$(Val)), 0.84 (3H, d, J 7, $CH_3$(Val)); $\delta_C$ (75 MHz; $d_6$-DMSO) 174.4, 171.9, 154.1, 78.0, 57.1, 55.7, 51.6, 30.2, 28.0, 25.3, 24.6, 18.8, 17.9

EXAMPLE 6

N-tert-butoxycarbonyl glycyl glycine methyl ester (19)

N-tert-butoxycarbonyl glycine (10.57 g, 60.33 mmol) and glycine methyl ester hydrochloride (7.58 g, 60.4 mmol) were dissolved in DMF (60 mL). N,N-diisopropylethyl amine (7.80 g, 60.4 mmol) and HOBt hydrate (9.24 g, 60.3 mmol) dissolved in DMF (40 mL) were added. The solution was cooled to 0° C. (icebath) and EDC hydrochloride (12.72 g, 66.35 mmol) added in small portions. The reaction mixture was stirred for 15 hours before the solvent was evaporated. The residue was taken up in EtOAc (300 mL) and washed with 2 M aqueous $H_2SO_4$ (3×50 mL), 7.5% (w/w) aqueous $K_2CO_3$ (3×50 mL) and saturated brine (50 mL). The solution was dried with anhydrous $MgSO_4$ and the solvent evaporated affording the title compound as a clear liquid (10.34 g, 70%) with spectral characteristics in accordance with literature data[8]; $\delta_H$ (300 MHz; $d_6$-DMSO) 8.17 (1H, t, J 6, $NH(Gly_2)$), 6.97 (1H, t, J 6, $NH(Gly_1)$), 3.85 (2H, d, J 6, $C^\alpha H_2(Gly_2)$), 3.62 (3H, s, $OCH_3$), 3.57 (2H, d, J 6, $C^\alpha H_2(Gly_1)$), 1.38 (9H, s, $(CH_3)_3$); $\delta_C$ (75 MHz; $d_6$-DMSO) 170.2, 169.9, 155.7, 78.0, 51.6, 42.9, 40.4, 28.1; m/z (ESI) 269.1110 ($[M+Na]^+$; $C_{10}H_{18}N_2O_5$ requires 269.1113)

EXAMPLE 7

Glycyl glycine methyl ester trifluoroacetate (21)

N-tert-butoxycarbonyl glycyl glycine methyl ester 19 (9.20 g, 37.4 mmol) was dissolved in a 50% (v/v) solution of TFA in $CH_2Cl_2$ (120 mL) at room temperature. The reaction mixture was stirred for 1 h 30 min before the solvent and bulk of excess TFA were evaporated. The residue was washed with $Et_2O$ (3×50 mL) and $CH_2Cl_2$ (50 mL) and dried affording the title compound as a slightly reddish viscous liquid in quantitative yield and with spectral characteristics in accordance with literature data.[9]; $\delta_H$ (300 MHz; $d_6$-DMSO) 8.91 (1H, t, J 6, NH), 8.20 (3H, br s, $NH_3^+$), 3.96 (2H, d, J 6, $C^\alpha H_2(Gly_2)$), 3.67-3.59 (5H, m, $C^\alpha H_2(Gly_1)/OCH_3$); $^{13}$C-NMR (75 MHz, $d_6$-DMSO): $\delta_C$ 169.9, 166.7, 158.7 (q, $J_{CF}$ 33), 116.4 (q, $J_{CF}$ 294), 54.9, 51.8, 40.6; m/z (ESI) 147.0769 ($M^+$; $C_5H_{11}N_2O_3$ requires 147.0769)

REFERENCES

1 A. Zhang, Y. Guo, Chem. Eur. J. 2008, 14(29), 8939-8946.
2 H. N. Gopi, R. S. Roy, S. R. Raghothama, I. L. Karle, P. Balaram, Helv. Chim. Acta, 2002, 85(10), 3313-3330.
3 A. K. Boal, I. Guryanov, A. Moretto, M. Crisma, E. L. Lanni, C. Toniolo, R. H. Grubbs, D. J. O'Leary, J. Am. Chem. Soc., 2007, 129(22), 6986-6987.
4 H. E. Blackwell, J. D. Sadowsky, R. J. Howard, J. N. Sampson, J. A. Chao, W. E. Steinmetz, D. J. O'Leary, R. H. Grubbs, J. Org. Chem., 2001, 66(16), 5291-5302.
5 G. DeWall, Chemical & Engineering News, 1982, 60(37), 5, 43.
6 J. Buckley, R. L. Webb, T. Laird, R. J. Ward, Chemical & Engineering News, 1982, 60(28), 5.
7 F. Albericio, M. A. Bailen, R. Chinchilla, D. J. Dodsworth, C. Najera, Tetrahedron, 2001, 57(47), 9607-9613.
8 R. K. Olsen, K. Ramasamy, J. Org. Chem. 1985, 50(13), 2264-2271.
9 G. Guichard, N. Benkirane, R. Graff, S. Muller, J. P. Briand, Peptide Research, 1994, 7(6), 308-321.

EXAMPLE 8

L-valyl L-valine methyl ester trifluoroacetate (6)

N-tert-butoxycarbonyl L-valyl L-valine methyl ester (4) (10.07 g, 30.48 mmol, 1.00 eq.) was treated with a 50% (v/v) TFA solution in $CH_2Cl_2$ for 2 hours at room temperature. The solvent and bulk of excess TFA were evaporated affording a clear, crystalline solid which contained TFA as judged by $^1$H-NMR. Small portions of purified $CHCl_3$ (i.e. without EtOH as stabiliser) were added and evaporated under reduced pressure four times resulting in an off-white solid. The solid was washed with $Et_2O$ (3×50 mL) and dried under reduced pressure affording a white solid (10.20 g, 97%). The compound has been mentioned in the literature, but spectral data was not provided[55]; $\delta_H$ (300 MHz; $d_6$-DMSO) 8.62 (1H, d, J 7, NH), 8.17 (3H, br s, $NH_3^+$), 4.19 (1H, dd, J 7 and 6, $C^\alpha H(Val_2)$), 3.75 (1H, br d, J 5, $C^\alpha H(Val_1)$), 3.64 (3H, s, $OCH_3$), 2.16-2.01 (2H, m, $CH(CH_3)_2$), 0.96-0.90 (12H, m, $CH(CH_3)_2$); $\delta_C$ (75 MHz; $d_6$-DMSO) 171.4, 168.4, 158.4 (q, $J_{CF}$ 31), 117.1 (q, $J_{CF}$ 297) 57.7, 56.9, 51.7, 29.9, 29.6, 18.8, 18.1, 18.1, 17.4; m/z (ESI) 231.1710 ($M^+$; $C_{11}H_{23}N_2O_3$ requires 231.1708)

EXAMPLE 9

α,α-Dimethylglycyl L-valine methyl ester trifluoroacetate (7)

A 50% (v/v) solution of TFA in $CH_2Cl_2$ (350 mL) was added to N-tert-butoxycarbonyl α,α-dimethylglycyl L-valine methyl ester (5) (33.50 g, 0.1059 mol) at room temperature and the reaction mixture stirred for 2 hours. The solvent and bulk of excess TFA were removed under reduced pressure. The residue was washed with $Et_2O$ (3×200 mL) and dried under reduced pressure affording a clear oil. Dichloromethane (3×200 mL) was added and evaporated under reduced pressure affording a sticky white solid (28.51 g, 82%); $\delta_H$ (300 MHz; $d_6$-DMSO) 8.42 (1H, d, J 8, NH), 8.26 (3H, br s, $NH_3^+$), 4.17 (1H, dd, J 8 and 8, $C^\alpha H$(Val)), 3.64 (3H, s, OCH$_3$), 2.16-2.05 (1H, m, CH(CH$_3$)$_2$), 1.52 (3H, s, CH$_3$ (Aib)), 1.50 (3H, s, CH$_3$(Aib)), 0.91 (3H, d, J 6, CH$_3$(Val)), 0.88 (3H, d, J 6, CH$_3$(Val)); δ$_C$ (75 MHz; d$_6$-DMSO) 172.0, 171.6, 158.1 (q, Jc$_F$ 32), 116.9 (q, J$_{CF}$ 297), 58.3, 56.5, 51.7, 29.5, 23.2, 23.1, 19.0, 18.6; m/z (ESI) 217.1556 (M$^+$; C$_{10}$H$_{21}$N$_2$O$_3$ requires 217.1552)

EXAMPLE 10

N-tert-butoxycarbonyl O-allyl L-seryl L-valyl L-valine methyl ester (8)

N-tert-butoxycarbonyl O-allyl L-serine (3) (11.31 g, 46.10 mmol) was dissolved in 40 mL DMF. A solution of L-valyl L-valine methyl ester.trifluoroacetate 6 (15.87 g, 46.09 mmol) and N,N-diisopropylethyl amine (5.96 g, 46.1 mmol) in 60 mL DMF was added in one portion and the solution cooled to 0° C. (icebath). HOBt hydrate (7.06 g, 46.1 mmol) was added. Finally, EDC hydrochloride (9.72 g, 50.7 mmol) was added together with 30 mL DMF. The reaction mixture was stirred for 22 hours before the solvent was evaporated. The residue was taken up in 250 mL EtOAc and washed with 2 M aqueous H$_2$SO$_4$ (3×100 mL), 7.5% (w/w) aqueous K$_2$CO$_3$ (3×100 mL) and saturated brine (100 mL). The solution was dried with anhydrous MgSO$_4$ and the solvent evaporated affording an off-white solid (19.82 g, 94%); δ$_H$ (300 MHz; d$_6$-DMSO) 8.18 (1H, d, J 8, NH(Val$_x$)), 7.62 (1H, d, J 9, NH(Val$_y$)), 7.03 (1H, d, J 8, NH(Ser(All))), 5.83 (1H, ddt, J 5, 10 and 17, CH=CH$_2$), 5.23 (1H, ddt, J 1, 3 and 17, CH=CHH), 5.11 (1H, ddt, J 1, 3 and 10, CH=CHH), 4.34 (1H, dd, J 7 and 9, C$^α$H(Val$_y$)), 4.22-4.17 (1H, m, C$^α$H(Ser(All))), 4.13 (1H, dd, J 6 and 8, C$^α$H(Val$_x$)), 3.92 (2H, dt, J 1 and 5, CH$_2$CH=CH$_2$), 3.61 (3H, s, OCH$_3$), 3.53-3.49 (2H, m, CH$_2$), 2.11-1.86 (2H, m, CH(CH$_3$)$_2$), 1.38 (9H, s, (CH$_3$)$_3$), 0.90-0.79 (12H, m, CH$_3$); δ$_C$ (75 MHz; d$_6$-DMSO) 171.6, 171.0, 169.5, 155.1, 134.9, 116.3, 78.2, 70.9, 69.5, 57.4, 56.8, 54.5, 51.4, 31.1, 29.5, 28.0, 18.9, 18.8, 18.1, 17.7; m/z (ESI) 480.2666 ([M+Na]$^+$; C$_{22}$H$_{39}$N$_3$O$_7$Na requires 480.2685)

EXAMPLE 11

O-allyl L-seryl L-valyl L-valine methyl ester (9)

N-tert-butoxycarbonyl O-allyl L-seryl L-valyl L-valine methyl ester (8) (6.80 g, 14.9 mmol) was stirred in formic acid (70 mL) at room temperature for 9 hours and the formic acid evaporated. The residue was diluted with 110 mL water and the aqueous solution washed with Et$_2$O (3×30 mL). The pH was adjusted to pH 9 by addition of solid K$_2$CO$_3$ and the resulting solution extracted with EtOAc (3×55 mL). The combined organic extracts were washed with saturated brine (30 mL) and dried with anhydrous MgSO$_4$. The solvent was evaporated affording a white solid (4.35 g, 82%); δ$_H$ (200 MHz; do-DMSO) 8.26 (1H, d, J 8, NH(Val$_x$)) 8.03 (1H, d, J 9, NH(Val$_y$)), 5.85 (1H, ddt, J 5, 10 and 17, CH=CH$_2$), 5.24 (1H, ddt, J 1, 3 and 17, CH=CHH), 5.12 (1H, ddt, J 1, 3 and 10, CH=CHH), 4.36 (1H, dd, J 6 and 9, C$^α$H(Val$_y$)), 4.12 (1H, dd, J 6 and 8, C$^α$H(Val$_x$)), 3.93 (2H, dt, J 1 and 5, CH$_2$CH=CH$_2$), 3.61 (3H, s, OCH$_3$), 3.49 (2H, d, J 5, CH$_2$,), 3.43-3.39 (1H, m, C$^α$H(Ser(All))), 2.38 (2H, br s, NH$_2$), 2.12-1.86 (2H, m, CH(CH$_3$)$_2$), 0.91-0.78 (12H, m, CH$_3$)

EXAMPLE 12

N-tert-butoxycarbonyl L-prolyl L-prolyl O-allyl L-seryl L-valyl L-valine methyl ester (10) (SEQ ID NO: 5)

N-tert-butoxycarbonyl L-prolyl L-proline 2 (3.80 g, 12.2 mmol) and O-allyl L-seryl L-valyl L-valine methyl ester 9 (4.35 g, 12.2 mmol) were in DMF (25 mL) and the solution cooled to 0° C. HOBt hydrate (1.87 g, 12.2 mmol) was added under stirring. EDC hydrochloride (2.57 g, 13.4 mmol) was added to the reaction mixture in small portions. The reaction mixture was stirred overnight and the solvent evaporated. The residue was taken up in EtOAc (50 mL) and washed with 2M HCl (3×25 mL), 7.5% (w/w) K$_2$CO$_3$ (3×25 mL) and saturated brine (20 mL). The solution was dried with anhydrous MgSO$_4$ and the solvent evaporated affording the title compound as a white solid (7.34 g, 93%); δ$_H$ (300 MHz; d$_6$-DMSO) 8.10 (1H, d, J 8, NH(Val$_x$)), 7.98 (1H, d, J 8, NH(Ser(All))), 7.60 (1H, d, J 9, NH(Val$_x$), rotomer 1), 7.59 (1H, d, J 9, NH(Val$_y$), rotomer 2), 5.83 (1H, ddt, J 5, 11 and 17, CH=CH$_2$), 5.24 (1H, ddt, J 1, 3 and 17, CH=CHH), 5.14-5.09 (1H, m, CH=CHH), 4.46-4.37 (3H, m, C$^α$H(Pro$_1$)/C$^α$H(Pro$_2$)/C$^α$H(Ser(All))), 4.32 (1H, dd, J 7 and 9, C$^α$H(Val$_y$)), 4.15-4.10 (1H, m, C$^α$H(Val$_x$)), 3.93 (2H, m, J 1 and 5, CH$_2$CH=CH$_2$), 3.67-3.50 and 3.36-3.24 (6H, m, C$^δ$H$_2$(Pro$_1$)/C$^δ$H$_2$(Pro$_2$)/CH$_2$(Ser(All))), 3.61 (3H, s, OCH$_3$), 2.26-1.71 (10H, m, CH$_2$(Pro)/CH(CH$_3$)$_2$), 1.37 (9H, s, (CH$_3$)$_3$, rotomer 1), 1.30 (9H, s, (CH$_3$)$_3$, rotomer 2), 0.89-0.80 (12H, m, CH$_3$); δ$_C$ (75 MHz; d$_6$-DMSO) 171.6, 171.5, 171.3, 171.1, 170.9, 170.4, 169.1, 169.1, 153.3, 152.9, 134.8, 116.5, 78.3, 78.1, 71.1, 69.3, 59.1, 57.4, 57.2, 56.9, 52.9, 51.4, 46.5, 46.4, 46.3, 46.3, 30.9, 30.6, 29.6, 29.5, 29.4, 28.7, 28.5, 28.1, 27.9, 24.4, 24.3, 23.6, 23.0; m/z (ESI) 674.3737 ([M+Na]$^+$; C$_{32}$H$_{53}$N$_5$O$_9$Na requires 674.3741)

EXAMPLE 13

N-tert-butoxycarbonyl O-allyl L-seryl α,α-dimethylglycyl L-valine methyl ester (12)

α,α-Dimethylglycyl L-valine methyl ester trifluoroacetate 7 (19.20 g, 58.13 mmol) was dissolved in DMF (100 mL). N-tert-butoxycarbonyl O-allyl L-serine 3 (14.25 g, 58.12 mmol) and then N,N-diisopropylethyl amine (7.51 g, 58.1 mmol) were added and the solution cooled to 0° C. (icebath). HOBt hydrate (8.91 g, 58.2 mmol) and then EDC hydrochloride (12.26 g, 63.95 mmol) were added together with an additional 70 mL DMF. The reaction mixture was stirred for 22 hours before the solvent was evaporated. The residue was taken up in EtOAc (350 mL) and washed with 2 M aqueous H$_2$SO$_4$ (3×130 mL), 7.5% (w/w) aqueous K$_2$CO$_3$ (3×130 mL) and saturated brine (130 mL). The solution was dried with anhydrous MgSO$_4$ and the solvent evaporated affording an off-white solid. $^1$H-NMR indicated 10-15% epimerization. The residue was recrystallized twice from ethyl acetate/hexane (4:1) to give the title compound as a stereopure off-white solid (20.15 g, 78% (sum of diastereomers)/13.49 g, 52%); δ$_H$ (300 MHz; d$_6$-DMSO) 8.01 (1H, s, NH(Aib)), 7.29 (1H, d, J 8, NH(Val)), 6.89 (1H, d, J 7, NH(Ser(All))), 5.92-5.79 (1H, m, CH=CH$_2$), 5.29-5.22 (1H, m, CH=CHH), 5.15-5.11 (1H, m, CH=CHH), 4.18-4.12 (2H, m, C$^α$H(Ser(All))/C$^α$H(Val)), 3.97-3.94 (2H, m, CH$_2$CH=CH$_2$), 3.62 (3H, s, OCH$_3$), 3.57-3.46 (2H, m, CH$_2$), 2.08-1.93 (1H, m, CH(CH$_3$)$_2$), 1.38 (9H, s, (CH$_3$)$_3$), 1.37 (3H, s, CH$_3$(Aib)), 1.35 (3H, s, CH$_3$(Aib)), 0.83 (3H, d, J 7, CH$_3$(Val)), 0.82 (3H, d, J 7, CH$_3$(Val)); δ$_C$ (75 MHz; d$_6$-DMSO) 173.8, 171.7, 169.5, 155.2, 134.8, 116.3, 78.2, 70.9, 69.4, 57.4, 56.1, 54.3, 51.5, 29.9, 28.0, 25.6, 23.8, 18.8, 18.1; m/z 466.2514 ([M+Na]$^+$; C$_{21}$H$_{37}$N$_3$O$_7$Na requires 466.2529)

EXAMPLE 14

N-tert-butoxycarbonyl O-benzyl L-seryl L-valyl L-valine methyl ester (13)

L-valyl L-valine methyl ester trifluoroacetate 6 (11.62 g, 33.75 mmol) was dissolved in 60 mL DMF. N-tert-butoxycarbonyl O-benzyl L-serine 14 (9.97 g, 33.8 mmol) was added together with 10 mL DMF. The solution was cooled to 0° C. (icebath) before N,N-diisopropylethyl amine (4.36 g, 33.7 mmol), HOBt hydrate (5.17 g, 33.8 mmol) and EDC hydrochloride (7.12 g, 37.1 mmol) were added together with an additional 30 mL DMF. The reaction mixture was stirred overnight and the solvent evaporated. The residue was taken up in 200 mL EtOAc and washed with 2M aqueous $H_2SO_4$ (3×80 mL), 7.5% (w/w) aqueous $K_2CO_3$ (3×80 mL) and saturated brine (80 mL). The solution was dried with anhydrous $MgSO_4$ and the solvent evaporated affording a white solid (16.22 g, 95%); $\delta_H$ (300 MHz; $d_6$-DMSO) 8.20 (1H, d, J 8, NH(Val$_x$)), 7.65 (1H, d, J 9, NH(Val$_y$)), 7.35-7.23 (5H, m, Ph), 7.08 (1H, d, J 8, NH(Ser(Bn)), 4.46 (2H, s, $CH_2Ph$), 4.35 (1H, dd, J 7 and 9, C$^\alpha$H(Val$_y$)), 4.25 (1H, m, C$^\alpha$H(Ser(Bn))), 4.12 (1H, dd, J 6 and 8, C$^\alpha$H(Val$_x$)), 3.63-3.54 (2H, m, $CH_2$), 3.60 (3H, s, $OCH_3$), 2.07-1.89 (2H, m, $CH(CH_3)_2$), 1.38 (9H, s, $(CH_3)_3$), 0.88-0.80 (12H, m, $CH_3$); $\delta_C$ (75 MHz; $d_6$-DMSO) 171.6, 171.0, 169.4, 155.1, 138.0, 128.0, 127.3, 127.3, 78.2, 71.9, 69.8, 57.4, 56.8, 54.5, 51.4, 31.1, 29.5, 28.0, 18.9, 18.7, 18.2, 17.7; m/z (ESI) 530.2824 ([M+Na]$^+$; $C_{26}H_{41}N_3O_7Na$ requires 530.2842)

EXAMPLE 15

N-tert-butoxycarbonyl O-allyl L-seryl L-valyl L-valine (15)

N-tert-butoxycarbonyl O-allyl L-seryl L-valyl L-valine methyl ester (8) (10.21 g, 22.31 mmol) was dissolved in THF (170 mL). The solution was cooled to 0° C. (icebath). LiOH monohydrate (1.03 g, 24.6 mmol) was dissolved in de-ionized water (85 mL) and the solution cooled to 0° C. The solution was then added dropwise to the solution of 8 over 20 min. The reaction mixture was stirred for an additional 2 h 40 min at 0° C. Solid $NaHCO_3$ (3.75 g, 44.6 mmol) was added and the mixture stirred for 5 min before the THF was evaporated. The solution was diluted with water (170 mL), washed with $Et_2O$ (2×170 mL), acidified to pH 2 by addition of 2 M aqueous $H_2SO_4$ and extracted with EtOAc (3×250 mL). The combined organic fractions were dried with anhydrous $MgSO_4$ and the solvent evaporated affording the title compound as a white solid (7.00 g, 71%); $\delta_H$ (300 MHz; $d_6$-DMSO) 12.53 (1H, br s, COOH), 8.00 (1H, d, J 8, NH (Val$_x$)), 7.62 (1H, d, J 9, NH(Val$_y$)), 7.02 (1H, d, J 8, NH (Ser(All))), 5.84 (1H, ddt, J 5, 10 and 17, CH=$CH_2$), 5.23 (1H, ddt, J 1, 3 and 17, CH=CHH), 5.12 (1H, ddt, J 1, 3 and 10, CH=CHH), 4.34 (1H, dd, J 7 and 9, C$^\alpha$H(Val$_y$)), 4.21-4.15 (1H, m, C$^\alpha$H(Ser(All))), 4.10 (1H, dd, J 6 and 8, C$^\alpha$H (Val$_x$)), 3.92 (2H, dt, J 1 and 5, $CH_2CH=CH_2$), 3.59-3.45 (2H, m, $CH_2$), 2.06-1.91 (2H, m, $CH(CH_3)_2$), 1.38 (9H, s, $(CH_3)_3$), 0.90-0.80 (12H, m, $CH_3$); $\delta_C$ (75 MHz; $d_6$-DMSO) 172.6, 170.9, 169.5, 155.1, 134.9, 116.3, 78.2, 71.0, 69.5, 57.2, 56.9, 54.6, 31.1, 29.6, 28.1, 19.0, 19.0, 17.9, 17.7; m/z (ESI) 466.2518 ([M+Na]$^+$; $C_{21}H_{37}N_3O_7Na$ requires 466.2529)

EXAMPLE 16

N-tert-butoxycarbonyl O-allyl L-seryl α,α-dimethylglycyl L-valine (16)

N-tert-butoxycarbonyl O-allyl L-seryl α,α-dimethylglycyl L-valine methyl ester 12 (8.56 g, 19.3 mmol) was dissolved in THF (150 mL). The solution was cooled to 0° C. (icebath). LiOH monohydrate (0.891 g, 21.2 mmol) was dissolved in de-ionized water (75 mL) and the solution cooled to 0° C. The solution was added dropwise to the solution of 12 over 20 min. The reaction mixture was stirred for an additional 2 h 40 min before solid $NaHCO_3$ (3.24 g, 38.6 mmol) was added. The mixture was stirred for 5 min and the bulk of THF evaporated. The solution was diluted with water (150 mL), washed with $Et_2O$ (2×150 mL), acidified to pH 2 by addition of 2 M aqueous $H_2SO_4$ and extracted with EtOAc (3×300 mL). The combined organic fractions were dried with anhydrous $MgSO_4$ and the solvent evaporated affording the title compound as a white solid (7.30 g, 88%); $\delta_H$ (300 MHz; $d_6$-DMSO) 12.62 (1H, br s, COOH), 8.01 (1H, s, NH(Aib)), 7.12 (1H, d, J 9, NH(Val)), 6.85 (1H, d, J 8, NH(Ser(All))), 5.92-5.79 (1H, m, CH=$CH_2$), 5.29-5.21 (1H, m, CH=CHH), 5.15-5.10 (1H, m, CH=CHH), 4.19-4.10 (2H, m, C$^\alpha$H(Ser(All))/C$^\alpha$H(Val)), 3.94 (2H, dt, J 1 and 5, $CH_2CH=CH_2$), 3.57-3.45 (2H, m, $CH_2$), 2.08-1.97 (1H, m, $CH(CH_3)_2$), 1.38 (12H, s, $CH_3(Aib)/(CH_3)_3$), 1.35 (3H, s, $CH_3(Aib)$), 0.84 (3H, d, J 7, $CH_3(Val)$), 0.81 (3H, d, J 7, $CH_3(Val)$); $\delta_C$ (75 MHz; $d_6$-DMSO): 173.6, 172.7, 169.5, 155.1, 134.9, 116.3, 78.2, 70.9, 69.5, 57.0, 56.1, 54.4, 30.1, 28.1, 25.7, 23.8, 19.0, 17.8; m/z (ESI) 452.2357 ([M+Na]$^+$; $C_{20}H_{35}N_3O_7Na$ requires 452.2372)

EXAMPLE 17

N-tert-butoxycarbonyl O-benzyl L-seryl L-valyl L-valine (17)

N-tert-butoxycarbonyl O-benzyl L-seryl L-valyl L-valine methyl ester 13 (14.60 g, 28.76 mmol) was dissolved in THF (220 mL) and the solution cooled to 0° C. (icebath). LiOH monohydrate (1.33 g, 31.7 mmol) was dissolved in de-ionized water (110 mL). The solution was cooled to 0° C. (icebath) and added dropwise to the solution of 13 over 25 min. The reaction mixture was stirred for an additional 2 h 35 min before solid $NaHCO_3$ (4.83 g, 57.5 mmol) was added and the bulk of THF evaporated. The solution was diluted with water (220 mL) and washed with $Et_2O$ (2×220 mL). The solution was then acidified to pH 2 by addition of 2 M aqueous $H_2SO_4$ and extracted with EtOAc (3×350 mL). The combined organic fractions were dried with anhydrous $MgSO_4$ and the solvent evaporated affording a slightly yellowish liquid. The residue was redissolved in EtOAc and precipitated by addition of hexane. The solvent was decanted off and the residue dried affording the title compound as an off-white solid (5.95 g, 42%); $\delta_H$ (200 MHz; $d_6$-DMSO) 12.52 (1H, br s, COOH), 8.03 (1H, d, J 8, NH(Val$_x$)), 7.65 (1H, d, J 9, NH(Val$_y$)), 7.36-7.23 (5H, m, Ph), 7.10 (1H, d, J 8, NH(Ser(Bn)), 4.46 (2H, s, $CH_2Ph$), 4.36 (1H, dd, J 7 and 9, C$^\alpha$H(Val$_y$)), 4.28-4.22 (1H, m, C$^\alpha$H(Ser(Bn))), 4.10 (1H, dd, J 6 and 8, C$^\alpha$H (Val$_x$)), 3.64-3.54 (2H, m, $CH_2$), 2.08-1.91 (2H, m, CH $(CH_3)_2$), 1.38 (9H, s, $(CH_3)_2$), 0.88-0.80 (12H, m, $CH_3$); $\delta_C$ (75 MHz; $d_6$-DMSO) 172.6, 170.9, 169.4, 155.1, 138.1, 128.0, 127.4, 127.3, 78.3, 71.9, 69.8, 57.2, 56.8, 54.6, 31.1, 29.5, 28.1, 19.0, 18.9, 18.0, 17.7; m/z (ESI) 516.2663 ([M+Na]$^+$; $C_{25}H_{39}N_3O_7Na$ requires 516.2685)

EXAMPLE 18

N-tert-butoxycarbonyl O-allyl L-seryl glycine methyl ester (18)

Purified N-tert-butoxycarbonyl O-allyl L-serine 3 (6.94 g, 28.3 mmol) was dissolved in 30 mL DMF and the solution cooled to 0° C. (icebath). Glycine methyl ester hydrochloride (3.55 g, 28.3 mmol) was suspended in 10 mL DMF and N,N-diisopropylethyl amine (3.66 g, 28.3 mmol) added. The suspension was then added in one portion to the solution of 3 together with an additional 5 mL DMF. HOBt hydrate (4.33 g, 28.3 mmol) was added. Finally, EDC hydrochloride (5.97 g, 31.1 mmol) was added together with an additional 10 mL DMF. The reaction mixture was stirred at 0° C. for 1 hour. In total the reaction mixture was stirred for 24 hours before the solvent was evaporated. The residue was taken up in 150 mL EtOAc and washed with 1 M aqueous $H_2SO_4$ (3×100 mL), 7.5% (w/w) aqueous $K_2CO_3$ (3×100 mL) and finally saturated brine (100 mL). The solution was dried with anhydrous $MgSO_4$ and the solvent evaporated affording a clear and slightly greenish/yellowish liquid (7.49 g, 84%); $\delta_H$ (200 MHz; $d_6$-DMSO) 8.31 (1H, t, J 6, NH(Gly)), 6.85 (1H, d, J 8, NH(Ser(All))), 5.86 (1H, ddt, J 5, 11 and 17, CH=$CH_2$), 5.29-5.11 (2H, m, CH=$CH_2$), 4.22 (1H, ddd, J 8 and 12, $C^\alpha$H(Ser(All))), 3.94 (2H, dt, J 1 and 5, $CH_2$CH=$CH_2$), 3.86 (1H, d, J 6, $C^\alpha$HH(Gly)), 3.83 (1H, d, J 6, $C^\alpha$HH(Gly)), 3.62 (3H, s, $OCH_3$), 3.56-3.44 (2H, m, $CH_2$), 1.38 (9H, s, $(CH_3)_3$); $\delta_C$ (50 MHz; $d_6$-DMSO) 170.3, 170.0, 155.1, 134.9, 116.3, 78.2, 70.9, 69.6, 54.1, 51.6, 40.5, 28.1; m/z (ESI) 339.1541 ([M+Na]$^+$; $C_{14}H_{24}N_2O_6Na$ requires 339.1532)

EXAMPLE 19

O-allyl L-seryl glycine methyl ester trifluoroacetate (20)

N-tert-butoxycarbonyl O-allyl L-seryl glycine methyl ester 18 (5.86 g, 18.3 mmol) was dissolved in $CH_2Cl_2$ (30 mL) and TFA (30 mL) added at room temperature. The reaction mixture was stirred for 2 hours before the solvent and bulk of excess TFA were evaporated affording a brownish liquid (7.50 g). The residue was washed with $Et_2O$ (2×25 mL), redissolved in $CH_2Cl_2$ (25 mL), the solvents evaporated and the residue dried under reduced pressure affording a brownish, viscous liquid (6.01 g, 98%); $\delta_H$ (300 MHz; $d_6$-DMSO) 9.02 (1H, t, J 6, NH), 8.33 (3H, br s, $NH_3^+$), 5.87 (1H, ddt, J 5, 10 and 17, CH=$CH_2$), 5.29 (1H, ddt, J 1, 2 and 17, CH=CHH), 5.21-5.14 (1H, m, CH=CHH), 4.10 (1H, m, $C^\alpha$H(Ser(All))), 4.00 (2H, ddd, J 1, 1 and 5, $CH_2$CH=$CH_2$), 3.95 (2H, d, J 6, $C^\alpha H_2$(Gly)), 3.78-3.67 (2H, m, $CH_2$), 3.64 (3H, s, $OCH_3$); $\delta_C$ (75 MHz; $d_6$-DMSO) 169.7, 167.0, 158.4 (q, $J_{CF}$ 32), 134.4, 116.7 (q, $J_{CF}$ 296), 71.4, 68.0, 54.9, 52.3, 51.8, 40.7; m/z (ESI) 217.1194 (M$^+$; $C_9H_{17}N_2O_4$ requires 217.1188)

EXAMPLE 20

N-tert-butoxycarbonyl O-allyl L-seryl L-valyl L-valyl O-allyl L-seryl glycine methyl ester (22) (SEQ ID NO: 1)

O-allyl L-seryl methyl ester trifluoroacetate 20 (7.03 g, 21.3 mmol), N-tert-butoxycarbonyl O-allyl L-seryl L-valyl L-valine 15 (9.45 g, 21.3 mmol) and N,N-diisopropylethyl amine (2.75 g, 21.3 mmol) were dissolved in $CH_2Cl_2$ (100 mL) and the solution cooled to 0° C. (icebath). HOBt hydrate (3.26 g, 21.3 mmol) and then EDC hydrochloride (4.49 g, 23.4 mmol) were added in small portions. The reaction mixture was stirred for 1 h 30 min at 0° C. after which the icebath was removed and the mixture stirred for 14 h 30 min. The volume was then increased by addition of $CH_2Cl_2$ (200 mL) and the mixture stirred for another 7 hours before the volume was increased to 400 mL. The suspension was washed with 2M aqueous $H_2SO_4$ (150+300+450 mL), 7.5% (w/w) aqueous $K_2CO_3$ (150+300+450 mL), saturated brine (400 mL) and water (400+600 mL). The suspension was then diluted with $CH_2Cl_2$ (1.5 L) and dried with 3 Å molecular sieves resulting in a slightly turbid solution.

The solvent was evaporated affording a slightly yellowish solid, which was recrystallised from EtOH affording the title compound as a white solid (12.12 g, 89%); $\delta_H$ (300 MHz; $d_6$-DMSO) 8.36 (1H, t, J 6, NH(Gly)), 7.98 (1H, d, J 8, NH(Ser($All_2$))), 7.90 (1H, d, J 9, NH($Val_x$)), 7.68 (1H, d, J 9, NH($Val_y$)), 7.02 (1H, d, J 8, NH(Ser($All_1$))), 5.90-5.77 (2H, m, CH=$CH_2$), 5.27-5.10 (4H, m, CH=$CH_2$), 4.55-4.49 (1H, m, $C^\alpha$H(Ser($All_2$))), 4.30-4.15 (3H, m, $C^\alpha$H($Val_x$)/$C^\alpha$H($Val_y$)/$C^\alpha$H(Ser($All_1$))), 3.95-3.91 (4H, m, $CH_2$CH=$CH_2$), 3.86-3.84 (2H, m, $C^\alpha H_2$(Gly)), 3.61 (3H, s, $OCH_3$), 3.56-3.46 (4H, m, $CH_2$), 2.02-1.89 (2H, m, CH($CH_3$)$_2$), 1.38 (9H, s, $(CH_3)_3$), 0.84-0.78 (12H, m, $CH_3$); $\delta_C$ (75 MHz; $d_6$-DMSO) 170.6, 169.9, 169.7, 169.5, 155.1, 134.9, 134.8, 116.5, 116.3, 79.8, 79.7, 78.2, 71.0, 69.5, 69.4, 57.4, 57.2, 57.2, 54.6, 54.5, 54.5, 52.3, 51.6, 40.5, 30.8, 30.3, 28.0, 19.0, 17.9, 17.8; m/z (ESI) 664.3526 ([M+Na]$^+$; $C_{30}H_{51}N_5O_{10}Na$ requires 664.3533)

EXAMPLE 21

N-tert-butoxycarbonyl O-allyl L-seryl α,α-dimethylglycyl L-valyl O-allyl L-seryl glycine methyl ester (23) (SEQ ID NO: 6)

O-allyl L-seryl glycine methyl ester trifluoroacetate 20 (4.42 g, 13.4 mmol) was dissolved in $CH_2Cl_2$ (40 mL) and N-tert-butoxycarbonyl O-allyl L-seryl α,α-dimethylglycyl L-valine 16 (5.75 g, 13.4 mmol) added. N,N-diisopropylethyl amine (1.73 g, 13.4 mmol) and HOBt hydrate (2.05 g, 13.4 mmol) were added and the solution cooled to 0° C. EDC hydrochloride (2.82 g, 14.7 mmol) was added in small portions together with 10 mL $CH_2Cl_2$. The reaction mixture was stirred for 1 h 30 min at 0° C. after which the icebath was removed and the mixture stirred for an additional 26 hours. The solution was diluted by addition of $CH_2Cl_2$ (60 mL) and washed with 2 M aqueous $H_2SO_4$ (3×90 mL), 7.5% (w/w) aqueous $K_2CO_3$ (3×90 mL) and saturated brine (90 mL). The volume was increased by addition of $CH_2Cl_2$, the solution dried with anhydrous $MgSO_4$ and the solvent evaporated affording a slightly orange solid (6.14 g, 73%); $\delta_H$ (300 MHz; $d_6$-DMSO) 8.25 (1H, t, J 6, NH(Gly)), 8.14 (1H, s, NH(Aib)), 7.88 (1H, d, J 8, NH(Ser(All))), 7.14 (1H, d, J 8, NH(Val)), 6.84 (1H, d, J 7, NH (Ser($All_1$))), 5.92-5.74 (2H, m, CH=$CH_2$), 5.28-5.11 (4H, m, CH=$CH_2$), 4.50 (1H, m, $C^\alpha$H (Ser($All_2$))), 4.17-4.09 (2H, m, $C^\alpha$H(Ser($All_1$))/$C^\alpha$H(Val)), 3.95 (4H, m, $CH_2$CH=$CH_2$), 3.85 (2H, d, J 6, $C^\alpha H_2$(Gly)), 3.61 (3H, s, $OCH_3$), 3.58-3.46 (4H, m, $CH_2$), 2.06-1.95 (1H, m, CH($CH_3$)$_2$), 1.38 (9H, s, $(CH_3)_3$), 1.35 (3H, s, $CH_3$(Aib)), 1.34 (3H, s, $CH_3$(Aib)), 0.83 (3H, d, J 7, $CH_3$(Val)), 0.78 (3H, d, J 7, $CH_3$(Val)); $\delta_C$ (75 MHz; $d_6$-DMSO) 173.9, 170.7, 169.9, 169.8, 169.7, 155.3, 134.8, 116.4, 116.3, 78.4, 71.0, 69.4, 58.2, 56.2, 54.8, 54.5, 52.5, 51.6, 40.6, 30.0, 28.0, 24.9, 24.7, 19.0, 17.8; m/z 650.3366 ([M+Na]$^+$; $C_{29}H_{49}N_5O_{10}Na$ requires 650.3377)

EXAMPLE 22

N-tert-butoxycarbonyl O-benzyl L-seryl L-valyl L-valyl glycyl glycine methyl ester (24) (SEQ ID NO: 7)

N-tert-butoxycarbonyl O-benzyl L-seryl L-valine 17 (2.20 g, 4.46 mmol) and glycyl glycine methyl ester trifluoroacetate 21 (1.16 g, 4.44 mmol) were dissolved in $CH_2Cl_2$ (15 mL). N,N-diisopropylethyl amine (0.57 g, 4.4 mmol) and HOBt hydrate (0.68 g, 4.4 mmol) were added and the solution cooled to 0° C. EDC hydrochloride (0.94 g, 4.9 mmol) was added slowly together with 5 mL $CH_2Cl_2$. The reaction mixture was stirred for 1 h 30 min at 0° C. after which the icebath was removed. The mixture was stirred for an additional 23 hours before the volume was increased by addition of $CH_2Cl_2$ (20 mL). The solution was washed with 2 M aqueous $H_2SO_4$ (3×30 mL), 7.5% (w/w) aqueous $K_2CO_3$ (3×30 mL) and saturated brine (30 mL). The volume of the solution was increased, the solution dried with anhydrous $MgSO_4$ and the solvent evaporated affording an off-white solid (2.14 g, 78%); $\delta_H$ (300 MHz; $d_6$-DMSO) 8.25-8.20 (2H, m, NH(Gly$_1$)/NH (Gly$_2$)), 7.93 (1H, d, J 8, NH(Val$_x$)), 7.70 (1H, d, J 9, NH(Val$_y$)), 7.35-7.25 (5H, m, Ph), 7.06 (1H, d, J 8, NH(Ser (Bn))), 4.47 (2H, s, $CH_2Ph$), 4.32-4.23 (2H, m, C$^\alpha$H(Ser (Bn))/C$^\alpha$H(Val)), 4.11 (1H, dd, J, C$^\alpha$H(Val)), 3.86 (2H, m, C$^\alpha$H$_2$(Gly)), 3.75 (2H, d, J 6, C$^\alpha$HH(Gly)), 3.62 (3H, s, OCH$_3$), 3.60-3.53 (2H, m, CH$_2$), 2.01-1.88 (2H, m, CH (CH$_3$)$_2$), 1.38 (9H, s, (CH$_3$)$_3$), 0.85-0.78 (12H, m, CH$_3$); $\delta_C$ (75 MHz; $d_6$-DMSO) 171.1, 170.9, 170.1, 169.6, 169.1, 155.2, 138.1, 128.0, 127.4, 127.3, 78.2, 71.9, 69.8, 58.1, 57.2, 54.5, 51.6, 41.6, 40.5, 30.8, 30.1, 28.1, 19.1, 18.2, 17.8; m/z (ESI) 644.3268 ([M+Na]$^+$; $C_{30}H_{47}N_5O_9$Na requires 644.3271)

EXAMPLE 23

Methyl 2-((3S,6S,9S,12S, E)-12-(tert-butoxycarbonylamino)-6,9-diisopropyl-5,8,11-trioxo-1,14-dioxa-4,7,10-triazacyclo octadec-16-ene-carboxamido)-acetate (25)

N-tert-butoxy carbonyl O-allyl L-seryl L-valyl L-valyl O-allyl L-seryl glycine methyl ester 22 (SEQ ID NO: 1) (0.642 g, 1.00 mmol) was dissolved in dry, degassed $CH_2Cl_2$ (225 mL). Grubbs' 2$^{nd}$ generation catalyst (0.085 g, 0.10 mmol) dissolved in dry, degassed $CH_2Cl_2$ (25 mL) was added by syringe and the reaction mixture stirred under argon atmosphere for 2 h 45 min. A second portion of Grubbs' 2$^{nd}$ generation catalyst (0.085 g, 0.10 mmol) dissolved in $CH_2Cl_2$ (20 mL) was then added and the reaction mixture stirred for an additional 4 h 45 min. Ethyl vinyl ether (1.5 mL) was added to quench the reaction/remaining catalyst. After stirring for 25 min the solvent was evaporated affording a dark residue. The residue was redissolved in a minimal amount of $CH_2Cl_2$ and purified by flash column chromatography (eluent: $CH_2Cl_2$/acetone (2:1)) affording the title compound as an off-white solid (0.256 g, 42%); $\delta_H$ (300 MHz; CDCl$_3$) 7.23-7.20 (2H, m, NH(Val$_x$)/NH(Gly)), 7.11 (1H, d, J 8, NH(Ser (All)$_2$)), 6.75 (1H, d, J 7, NH(Val$_y$)), 5.92-5.80 (2H, m, CH=CH), 5.35 (1H, d, J 6, NH(Ser(All)$_1$)), 4.71-4.65 (1H, m, C$^\alpha$H(Ser(All)$_2$)), 4.37 (1H, dd, J 6 and 12, CH(Ser(All)$_1$)), 4.18-4.11 (3H, m, CHHCH=CH/C$^\alpha$H(Val$_x$)/C$^\alpha$H(Val$_y$)), 4.08 (1H, d, J 6, C$^\alpha$HH(Gly)), 4.02-3.91 (5H, m, CHH(Ser(All)$_2$)/CH$_2$CH=CH/CHHCH=CH/CHH(Gly)), 3.77-3.69 (2H, m, CH$_2$(Ser(All)$_1$)), 3.73 (3H, s, OCH$_3$), 3.63 (1H, dd, J 5 and 9, CHH(Ser(All)$_2$)), 2.35-2.21 (2H, m, CH(CH$_3$)$_2$), 1.46 (9H, s, (CH$_3$)$_3$), 1.02-0.90 (12H, m, CH$_3$); $\delta_C$ (75 MHz; CDCl$_3$) 172.0, 171.5, 171.3, 170.0, 156.3, 130.7, 128.7, 80.8, 77.2, 71.2, 70.0, 68.9, 67.7, 60.5, 60.4, 54.3, 53.3, 52.2, 41.3, 29.9, 29.3, 28.2, 19.5, 19.5, 18.0, 17.3; m/z (ESI) 636.3209 ([M+Na]$^+$; $C_{28}H_{47}N_5O_{10}$Na requires 636.3220)

EXAMPLE 24

Methyl 2-((3S,6S,12S,E)-12-(tert-butoxycarbonylamino)-6-isopropyl-9,9-dimethyl-5,8,11-trioxo-1, 14-dioxa-4,7,10-triaza cyclooctadec-16-enecarboxamido)acetate (26)

N-tert-butoxy carbonyl O-allyl L-seryl α,α-dimethylglycyl L-valyl O-allyl L-seryl glycine methyl ester 23 (SKI ID NO: 6) (0.571 g, 0.910 mmol) was dissolved in dry $CH_2Cl_2$ (200 mL) and the solution degassed. Grubbs' 2$^{nd}$ generation catalyst (0.077 g, 0.091 mmol) was dissolved in dry, degassed $CH_2Cl_2$ (25 mL) and added to the solution of 23 by syringe. The reaction mixture was stirred under argon atmosphere for 3 hours. A new portion of Grubbs' 2$^{nd}$ generation catalyst (0.039 g, 0.046 mmol) dissolved in dry, degassed $CH_2Cl_2$ (10 mL) was then added. After stirring for 3 hours ethyl vinyl ether (1.0 mL) was added to quench the reaction/remaining catalyst. The reaction mixture was stirred for an additional 30 min before the solvent was evaporated. The residue was purified by flash column chromatography (eluent: $CH_2Cl_2$/acetone (2:1)) affording a glassy/transparent solid (0.286 g, 52%); $\delta_H$ (300 MHz; CDCl$_3$) 7.56-7.40 (2H, m, NH(Ser (All)$_2$)/NH(Gly)), 7.13 (1H, s, NH(Aib)), 6.93 (1H, d, J 5, NH(Val)), 5.81-5.65 (2H, m, CH=CH), 5.49 (1H, d, J 5, NH(Ser(All)$_1$)), 4.79-4.73 (1H, m, C$^\alpha$H(Ser(All)$_2$)), 4.25-4.19 (1H, m, C$^\alpha$H(Ser$_1$)), 4.11-4.00 (4H, m, C$^\alpha$H(Val)/C$^\alpha$HH (Gly)/CH$_2$CH=CH), 3.89-3.74 (6H, m, CH$_2$CH=CH/ C$^\alpha$HH(Gly)/CH$_2$(Ser(All)$_2$))/CHH(Ser$_1$)), 3.66 (3H, s, OCH$_3$), 3.59-3.49 (1H, m, CHH(Ser$_1$)), 2.42-2.25 (1H, m, CH(CH$_3$)$_2$), 1.47-1.41 (15H, m, CH$_3$(Aib)/(CH$_3$)$_3$), 1.00-0.92 (6H, m, CH$_3$(Val)); $\delta_C$ (75 MHz; CDCl$_3$) 175.6, 171.2, 171.0, 170.1, 169.9, 156.0, 131.0, 127.7, 80.7, 70.5, 69.5, 69.2, 67.0, 60.6, 57.3, 55.0, 53.8, 51.9, 41.1, 29.0, 28.1, 26.3, 23.7, 19.3, 17.4; m/z (ESI) 622.3054 ([M+Na]$^+$; $C_{27}H_{45}N_5O_{10}$Na requires 622.3064)

EXAMPLE 25

(3S,6S,9S,12S,E)-6,9-diisopropyl-3-(2-methoxy-2-oxoethyl carbamoyl)-5,8,11-trioxo-1,14-dioxa-4,7, 10-triazacycloocta dec-16-en-12-aminium 2,2,2-trifluoroacetate (27)

Cyclic pentapeptide 25 (0.403 g, 0.657 mmol) was dissolved in a 50% (v/v) solution of TFA in $CH_2Cl_2$ (10 mL) at room temperature. The reaction mixture was stirred for 2 hours before the solvent and excess TFA were evaporated affording an off-white solid. Dichloromethane (10 mL) was added and evaporated and the residue washed with Et$_2$O (2×5 mL) to give the title compound as a slightly off-white solid (0.392 g, 95%); $\delta_H$ (300 MHz; $d_6$-DMSO) 8.76 (1H, d, J 9, NH(Val$_x$)), 8.58 (1H, t, J 6, NH(Gly)), 8.37-8.22 (4H, m, NH(Ser(All)$_2$)/NH$_3^+$), 7.31 (1H, d, J 8, NH(Val$_y$)), 5.80-5.67 (2H, m, CH=CH), 4.84-4.77 (1H, m, C$^\alpha$H(Ser(All)$_2$)), 4.32 (1H, dd, J 6 and 8, C$^\alpha$H(Val$_y$)), 4.13-3.93 (6H, m, CH$_2$CH=CH$_2$/C$^\alpha$H(Val$_x$)/C$^\alpha$H(Ser(All)$_1$)), 3.90-3.87 (2H, m, C$^\alpha$H$_2$(Gly)), 3.70 (1H, dd, J 4 and 10, CHH(Ser(All)$_1$)), 3.62 (3H, s, OCH$_3$), 3.55-3.42 (3H, m, CH$_2$(Ser(All)$_2$)/CHH (Ser(All)$_1$)), 2.10-1.89 (2H, m, CH(CH$_3$)$_2$), 0.91-0.83 (12H, m, CH$_3$); $\delta_C$ (75 MHz; $d_6$-DMSO) 169.9, 169.8, 169.6, 169.5, 166.3, 130.6, 128.6, 70.9, 68.9, 68.7, 67.5, 59.8, 56.9, 52.6, 51.6, 50.8, 40.5, 31.4, 30.3, 19.2, 18.7, 18.3, 18.2; m/z (ESI) 514.2868 (M$^+$; $C_{23}H_{40}N_5O_8$ requires 514.2876)

EXAMPLE 26

(3S,6S,12S,E)-6-isopropyl-3-(2-methoxy-2-oxoethylcarbamoyl)-9,9-dimethyl-5,8,11-trioxo-1,14-dioxa-4,7,10-triazacyclo octadec-16-en-12-aminium 2,2,2-trifluoroacetate (28)

Cyclic pentapeptide 26 (0.426 g, 0.710 mmol) was dissolved in a 50% (v/v) solution of TFA in $CH_2Cl_2$ (10 mL). The reaction mixture was stirred for 1 hour at room temperature before the solvent and bulk of excess TFA were evaporated. $Et_2O$ (10 mL) was added to the liquid residue, which resulted in precipitation of a white solid. After decanting off the $Et_2O$ the residue was washed with additional portions of $Et_2O$ (2×10 mL) and dried affording a white solid (0.309 g, 71%); $\delta_H$ (300 MHz; $d_6$-DMSO) 8.80 (1H, s, NH(Aib)), 8.49 (1H, t, J 6, NH(Gly)), 8.28 (3H, br s, $NH_3^+$), 8.13 (1H, d, J 8, NH(Ser(All)$_2$)), 7.11 (1H, d, J 7, NH(Val)), 5.84-5.72 (2H, m, CH=CH), 4.68-4.61 (1H, m, C$^\alpha$H(Ser(All)$_2$)), 4.24-4.03 (4H, m, C$^\alpha$H(Val)/$CH_2$CH=CH/CHHCH=CH), 3.96-3.91 (2H, m, C$^\alpha$H(Ser(All)$_1$)/CHHCH=CH), 3.88 (2H, dd, J 6 and 6, C$^\alpha$H$_2$(Gly)), 3.73 (1H, dd, J 4 and 10, CHH(Ser(All)$_1$)), 3.62 (3H, s, $OCH_3$), 3.54-3.39 (3H, m, $CH_2$(Ser(All)$_2$)/CHH(Ser(All)$_1$)), 2.04-1.93 (1H, m, CH(CH$_3$)$_2$), 1.43 (3H, s, $CH_3$(Aib)), 1.38 (3H, s, $CH_3$(Aib)), 0.83 (3H, s, $CH_3$(Val)), 0.81 (3H, s, $CH_3$(Val)); $\delta_C$ (75 MHz; $d_6$-DMSO) 172.8, 170.1, 169.8, 169.7, 165.8, 131.0, 129.9, 70.4, 68.9, 67.8, 66.4, 57.4, 56.5, 53.6, 52.5, 51.6, 40.5, 30.8, 26.7, 22.7, 18.8, 18.1; m/z (ESI) 500.2713 (M$^+$; $C_{22}H_{38}N_5O_8$ requires 500.2720)

EXAMPLE 27

(S)-tert-butyl 2-((R)-2-(3S,6S,9S,12S,E)-6,9-diisopropyl-3-(2-methoxy-2-oxoethylcarbamoyl)-5,8,11-trioxo-1,14-dioxa-4,7,10-triazacyclooctadec-16-en-12-ylcarbamoyl)pyrrolidine-1-carbonyl)pyrrolidine-1-carboxylate (29)

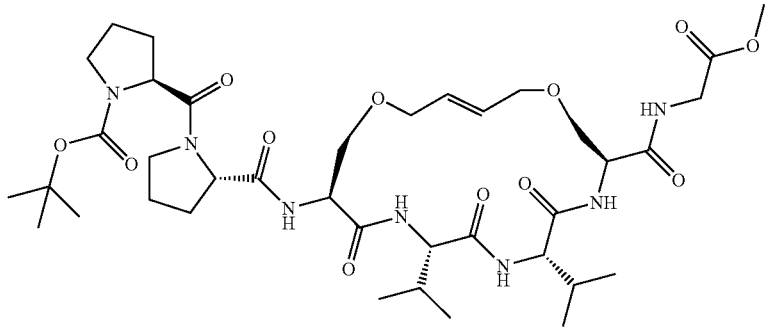 [SMILES: COC(=O)CNC(=O)[C@@H]1COC/C=C/COC[C@H](NC(=O)[C@@H]2CCCN2C(=O)[C@@H]2CCCN2C(=O)OC(C)(C)C)C(=O)N[C@@H](C(C)C)C(=O)N[C@@H](C(C)C)C(=O)N1]

Trifluoroacetate 27 (0.314 g, 0.500 mmol), N-tert-butoxycarbonyl L-prolyl L-proline 2 (0.157 g, 0.503 mmol) and HOBt hydrate (0.077 g, 0.50 mmol) were dissolved in $CH_2Cl_2$ (5 mL). N,N-diisopropylethyl amine (0.064 g, 0.50 mmol) dissolved in $CH_2Cl_2$ (1 mL) was added and the mixture stirred for 5 min. EDC hydrochloride (0.106 g, 0.553 mmol) was added in portions together with $CH_2Cl_2$ (4 mL). The reaction mixture was stirred for 1 hour at room temperature before $CH_2Cl_2$ (5 mL) was added. Stirring was continued for 21 hours after which the volume was increased to 50 mL by addition of $CH_2Cl_2$. The solution was washed with 1M aqueous $H_2SO_4$ (3×20 mL), 7.5% (w/w) $K_2CO_3$ solution (3×20 mL) and saturated brine (20 mL). The solution was dried with anhydrous $MgSO_4$ and the solvent evaporated affording the title compound as an off-white solid (0.316 g, 78%); $\delta_H$ (300 MHz; $CD_2Cl_2$) 7.93 (1H, d, J 7, NH(Ser(All)$_1$)), 7.77 (1H, d, J 5, NH(Val$_1$)), 7.36-7.31 (2H, m, NH(Ser(All)$_2$)/NH(Gly)), 6.80 (1H, d, J 6, NH(Val$_2$)), 5.93-5.73 (2H, m, CH=CH), 4.73-4.66 (1H, m, C$^\alpha$H(Ser(All)$_1$)), 4.64-4.58 (1H, m, C$^\alpha$H(Ser(All)$_2$)), 4.40 (1H, dd, J 8 and 8, C$^\alpha$H(Pro$_2$), 4.33-4.27 (1H, m, C$^\alpha$H(Pro$_1$), 4.20-3.83 (11H, m, C$^\alpha$H(Val$_1$)/C$^\alpha$H(Val$_2$)/C$^\alpha$H$_2$(Gly)/$CH_2$(Ser(All)$_1$)/CHH(Ser(All)$_2$)/$CH_2$CH=CH), 3.71-3.58 (3H, m, CHH(Ser(All)$_2$)/C$^\delta$H$_2$(Pro)), 3.69 (3H, s, $OCH_3$), 3.46-3.29 (2H, m, C$^\delta$H$_2$(Pro)), 2.45-2.19 (4H, m, $CH_2$(Pro)), 2.11-1.77 (6H, m, CH(CH$_3$)$_2$/$CH_2$(Pro)), 1.47 (9H, s, (CH$_3$)$_3$), 1.07-0.96 (12H, m, CH$_3$); $\delta_C$ (75 MHz; $CD_2Cl_2$) 173.9, 173.4, 172.5, 172.3, 172.0, 170.9, 170.5, 155.5, 132.8, 130.8, 81.6, 71.2, 70.7, 69.7, 67.3, 63.5, 63.1, 63.0, 61.2, 55.6, 54.6, 52.4, 47.7, 47.4, 41.8, 29.6, 29.5, 29.4, 29.4, 28.6, 26.7, 25.2, 19.8, 19.3, 19.0, 17.8; m/z (ESI) 830.4269 ([M+Na]$^+$; $C_{38}H_{61}N_7O_{12}Na$ requires 830.4275)

EXAMPLE 28

(S)-tert-butyl 2-((R)-2-(3S,6S,9S,12S,E)-6-isopropyl-3-(2-methoxy-2-oxoethylcarbamoyl)-9,9-dimethyl-5,8,11-trioxo-1,14-dioxa-4,7,10-triazacyclooctadec-16-en-12-ylcarbamoyl)pyrrolidine-1-carbonyl)pyrrolidine-1-carboxylate (30)

Tri-fluoroacetate 28 (0.238 g, 0.388 mmol), N-tert-butoxycarbonyl L-prolyl L-proline 2 (0.122 g, 0.391 mmol) and HOBt hydrate (0.059 g, 0.39 mmol) were dissolved in $CH_2Cl_2$ (5 mL). N,N-diisopropylethyl amine (0.050 g; 0.39 mmol) dissolved in $CH_2Cl_2$ (1 mL) was added and the mixture cooled to 0° C. (icebath). EDC hydrochloride (0.082 g, 0.43 mmol) was added in portions together with more $CH_2Cl_2$ (4 mL). The reaction mixture was stirred for 1 hour at 0° C., after which the icebath was removed and stirring continued for 24 h at room temperature. The volume was increased to 50 mL by addition of $CH_2Cl_2$ and the solution washed with 1M aqueous $H_2SO_4$ (3×20 mL), 7.5% (w/w) $K_2CO_3$ solution (3×20 mL) and saturated brine (20 mL). The solution was dried with anhydrous $MgSO_4$ and the solvent evaporated affording the title compound as a white solid (0.251 g, 82%); $\delta_H$ (300 MHz; $CD_2Cl_2$) 7.95 (1H, s, NH(Aib)), 7.87 (1H, d, J 7, NH(Ser(All)$_1$)), 7.59 (1H, d, J 9, NH(Ser(All)$_2$)), 7.46 (1H, t, J 6, NH(Gly)), 6.94-6.80 (1H, d, J 6, NH(Val)), 5.89-5.68 (2H, m, CH=CH), 4.67-4.57 (2H, m, C$^\alpha$H(Ser(All)$_2$)/C$^\alpha$H(Ser(All)$_1$)) 4.41 (1H, m, C$^\alpha$H(Pro$_2$)), 4.35-4.29 (1H, m, C$^\alpha$H(Pro$_1$)), 4.12-3.82 (10H, m, C$^\alpha$H(Val)/C$^\alpha$H$_2$(Gly)/$CH_2$(Ser(All)$_1$)/CHH (Ser(All)$_2$)/$CH_2$CH=CH), 3.70-3.58 (3H, m, CHH(Ser(All)$_2$)/C$^\delta$H$_2$(Pro)), 3.67 (3H, s, OCH$_3$), 3.50-3.29 (2H, m, C$^\delta$H$_2$(Pro)), 2.45-2.26 (3H, m, CH$_2$(Pro)), 2.11-1.76 (6H, m, CH(CH$_3$)$_2$/CH$_2$(Pro)), 1.48-1.35 (15H, m, CH$_3$(Aib)/(CH$_3$)$_3$), 1.05-0.97 (6H, m, CH$_3$(Val)); $\delta_C$ (75 MHz; CD$_2$Cl$_2$) 177.0, 173.7, 172.4, 172.0, 171.3, 170.9, 170.4, 155.6, 133.1, 130.4, 81.6, 71.1, 70.0, 69.5, 66.9, 63.5, 63.2, 61.6, 58.0, 54.9, 54.5, 52.4, 47.8, 47.4, 41.7, 29.8, 29.4, 29.3, 28.6, 27.3, 26.7, 25.3, 23.6, 19.6, 17.7; m/z (ESI) 816.4103 ([M+Na]$^+$; C$_{37}$H$_{59}$N$_7$O$_{12}$Na requires 816.4119)

EXAMPLE 29

N-tert-butoxycarbonyl L-prolyl L-prolyl O-allyl L-seryl L-valyl L-valyl O-allyl L-seryl glycine methyl ester (31) (SEQ ID NO: 2)

O-allyl L-seryl L-valyl L-valyl O-allyl L-seryl glycine methyl ester trifluoroacetate 32 (SEQ ID NO: 1) (0.524 g, 0.799 mmol), N-tert-butoxycarbonyl L-prolyl L-proline 2 (0.250 g, 0.800 mmol) and HOBt hydrate (0.122 g, 0.797 mmol) were dissolved in CH$_2$Cl$_2$ (5 mL). N,N-diisopropylethyl amine (0.103 g, 0.797 mmol) dissolved in CH$_2$Cl$_2$ (5 mL) was added. At this stage the reaction mixture turned into a gel. EDC hydrochloride (0.169 g, 0.882 mmol) was added in portions together with an additional 5 mL of CH$_2$Cl$_2$ and the reaction mixture vigorously stirred for 21 hours at room temperature. The volume was subsequently increased to 50 mL by addition of CH$_2$Cl$_2$. The solution was washed with 2M aqueous H$_2$SO$_4$ (3×20 mL), 7.5%. (w/w) K$_2$CO$_3$ solution (3×20 mL) and saturated brine (30 mL). The solution was dried with anhydrous MgSO$_4$ and the solvent evaporated affording the title compound as an off-white solid (0.489 g, 73%); $\delta_H$ (300 MHz; CDCl$_3$) 7.50-7.37 (3H, m, NH(Val$_x$)/NH(Gly)/NH(Ser(All)$_x$)), 7.12 and 6.85 (1H, d, J 6, NH(Ser(All)$_y$)), 7.02 (1H, d, J 5, NH(Val$_y$)), 5.89-5.71 (2H, m, CH=CH$_2$), 5.24-5.07 (4H, m, CH=CH$_2$), 4.83-4.76 (1H, m, C$^\alpha$H(Ser(All)$_x$)), 4.48-4.38 (3H, m, C$^\alpha$H(Ser(All)$_y$)/C$^\alpha$H(Pro$_x$)/C$^\alpha$H(Pro$_y$)), 4.31-4.27 (1H, m, C$^\alpha$H(Val$_y$)), 4.23-4.19 (1H, m, C$^\alpha$H(Val$_x$)), 4.09 (1H, dd, J 6 and 18, C$^\alpha$HH(Gly)), 3.99-3.92 (5H, m, C$^\alpha$HH(Gly)/CH$_2$CH=CH$_2$), 3.87-3.37 (8H, m, H$_2$(Ser(All)$_x$)/CH$_2$(Ser(All)$_y$)/C$^\delta$H$_2$(Pro$_x$)/C$^\delta$H$_2$(Pro$_y$)), 3.68 (3H, s, OCH$_3$), 2.34-1.81 (10H, m, CH$_2$(Pro$_x$)/CH$_2$(Pro$_y$)/CH(CH$_3$)$_2$), 1.44 and 1.36 (9H, s, (CH$_3$)$_3$), 1.02-0.85 (12H, m, CH$_3$); $\delta_C$ (75 MHz; CDCl$_3$) 172.8, 172.6, 171.9, 171.9, 171.8, 171.8, 171.7, 171.3, 171.1, 170.5, 170.4, 170.1, 170.1, 154.5, 153.3, 134.7, 134.6, 133.8, 133.6, 118.0, 117.6, 116.7, 116.6, 80.2, 79.7, 72.3, 72.0, 71.7, 69.5, 68.4, 62.1, 61.6, 61.0, 60.9, 60.1, 59.2, 57.7, 57.7, 55.1, 54.6, 53.2, 53.0, 52.0, 51.9, 47.3, 46.7, 46.5, 41.3, 30.6, 29.9, 29.8, 29.4, 28.9, 28.9, 28.4, 28.3, 25.5, 25.3, 24.5, 23.8, 19.4, 19.0, 18.9, 18.2, 18.1, 18.0, 17.9; m/z (ESI) 858.4575 ([M+Na]$^+$; C$_{40}$H$_{65}$N$_7$O$_{12}$Na requires 858.4588)

EXAMPLE 30

O-allyl L-seryl L-valyl L-valyl O-allyl L-seryl glycine methyl ester trifluoroacetate (32) (SEQ ID NO: 1)

N-tert-butoxycarbonyl O-allyl L-seryl L-valyl L-valyl O-allyl L-seryl glycine methyl ester 22 (SEQ ID NO: 1) (0.734 g, 1.14 mmol) was dissolved in a 50% (v/v) solution of TFA in CH$_2$Cl$_2$ (16 mL). The reaction mixture was stirred for 1 h 30 min before the solvent and bulk of excess TFA were evaporated affording an oil. Addition of Et$_2$O (25 mL) resulted in the precipitation of a white solid. The mixture was centrifuged and the Et$_2$O decanted off. The residue was washed with an additional 2×25 mL Et$_2$O and dried under reduced pressure overnight affording a fine white powder (0.719 g, 96%); $\delta_H$ (300 MHz; d$_6$-DMSO) 8.48 (1H, d, J 9, NH(Val$_x$)), 8.41 (1H, t, J 6, NH(Gly)), 8.24 (3H, br s, NH$_3$$^+$), 8.01-7.98 (2H, m, NH(Val$_y$)/NH(Ser(All)$_2$)), 5.90-5.77 (2H, m, CH=CH$_2$), 5.30-5.10 (4H, m, CH=CH$_2$), 4.56-4.50 (1H, m, C$^\alpha$H(Ser(All)$_2$)), 4.32 (1H, dd, J 7 and 9, C$^\alpha$H(Val$_x$)), 4.24 (1H, dd, J 7 and 8, C$^\alpha$H(Val$_y$)), 4.10 (1H, br s, C$^\alpha$H(Ser(All)$_1$)), 3.98-3.93 (4H, m, CH$_2$CH=CH$_2$), 3.86-3.84 (2H, m, C$^\alpha$H$_2$(Gly)), 3.72-3.52 (4H, m, CH$_2$(Ser(All)$_1$)/CH$_2$(Ser(All)$_2$)), 3.61 (3H, s, OCH$_3$), 2.08-1.89 (2H, m, CH(CH$_3$)$_2$), 0.88-0.80 (12H, m, CH$_3$); $\delta_C$ (75 MHz; d$_6$-DMSO) 170.6, 170.4, 169.9, 169.8, 166.2, 158.3 (q, J$_{CF}$ 37) 134.8, 134.4, 117.1, 116.9 (q, J$_{CF}$ 293), 116.5, 71.4, 71.0, 69.5, 68.3, 57.9, 57.6, 52.4, 52.2, 51.6, 40.6, 30.6, 30.4, 19.1, 18.1, 17.9; m/z (ESI) 542.3181 (M$^+$; C$_{25}$H$_{44}$N$_5$O$_8$ requires 542.3189)

EXAMPLE 31

N-tert-butoxycarbonyl L-prolyl L-prolyl O-benzyl L-seryl L-valyl L-valyl glycyl glycine methyl ester (33) (SEQ ID NO: 8)

O-benzyl L-seryl L-valyl L-valyl glycyl glycine methyl ester trifluoroacetate 34 (SEQ ID NO: 7) (0.364 g, 0.573 mmol), N-tert-butoxycarbonyl L-prolyl L-proline 2 (0.179 g, 0.573 mmol) and HOBt hydrate (0.088 g, 0.58 mmol) were dissolved in CH$_2$Cl$_2$ (4 mL). N,N-diisopropylethyl amine (0.074 g, 0.57 mmol) dissolved in CH$_2$Cl$_2$ (1 mL) was added and the mixture cooled to 0° C. (icebath). EDC hydrochloride (0.121 g, 0.631 mmol) was added in portions together with more CH$_2$Cl$_2$ (1 mL). The icebath was removed after 1 hour and the reaction mixture stirred for 22 hours at room temperature. The volume was increased to 40 mL by addition of CH$_2$Cl$_2$ and the solution washed with 2M aqueous H$_2$SO$_4$ (3×20 mL), 7.5% (w/w) K$_2$CO$_3$ solution (3×20 mL) and saturated brine (20 mL). The solution was dried with anhydrous MgSO$_4$ and the solvent evaporated affording the title compound as a slightly yellowish transparent/glassy solid (0.364 g, 78%); $\delta_H$(300 MHz; CDCl$_3$) 7.56-7.51 (1H, m, NH(Val$_x$)), 7.48-7.37 (2H, m, NH(Gly$_x$)/NH(Gly$_y$)), 7.32-7.18 (6H, m, Ph/NH(Ser(Bn)), rotomer 1), 6.90 (1H, d, J 8, NH(Val$_y$)), 6.82 (1H, d, NH(Ser(Bn)), rotomer 2), 4.52-4.27 (6H, m, C$^\alpha$H(Val$_y$)/C$^\alpha$H(Ser(Bn))/C$^\alpha$H(Pro$_x$)/C$^\alpha$H (Pro$_y$)/CH$_2$Ph), 4.21-4.11 (1H, m, C$^\alpha$H(Val$_x$)), 4.07-3.85 (4H, m, C$^\alpha$H$_2$(Gly)), 4.06-3.75 (3H, m, CH$_2$(Ser(Bn))/C$^\delta$HH(Pro$_x$)), 3.73-3.58 (1H, m, C$^\delta$HH(Pro$_y$)), 3.64 and 3.62 (3H, s, OCH$_3$), 3.52-3.23 (2H, m, C$^\delta$HH(Pro$_x$)/C$^\delta$HH(Pro$_y$)), 2.49-2.36 (1H, m, CH(CH$_3$)$_2$), 2.34-1.91 (6H, m, CH(CH$_3$)$_2$/CH$_2$(Pro)), 1.87-1.49 (3H, m, CH$_2$(Pro)), 1.40 and 1.33 (9H, s, (CH$_3$)$_3$), 1.03-0.98 (6H, m, CH$_3$(Val$_x$)), 0.93-0.89 (6H, m, CH$_3$(Val$_y$)); $\delta_C$ (75 MHz; CDCl$_3$) 174.2, 173.2, 172.8, 172.5, 172.0, 172.0, 171.9, 171.8, 171.8, 171.8, 154.4, 153.1, 146.0, 137.2, 136.8, 128.4, 128.3, 128.1, 127.9, 127.8, 127.6, 80.3, 73.6, 73.1, 68.4, 62.2, 61.8, 61.6, 59.7, 58.7, 57.6, 55.7, 55.2, 53.4, 51.9, 51.8, 47.4, 47.3, 46.7, 46.4, 43.1, 40.9, 30.4, 29.4, 29.2, 29.1, 28.9, 28.3, 28.2, 25.6, 25.3, 24.4, 23.6, 19.5, 19.1, 19.0, 18.6, 18.3, 17.5; m/z (ESI) 838.4308 ([M+Na]$^+$; C$_{40}$H$_{61}$N$_7$O$_{11}$Na requires 838.4326)

EXAMPLE 32

O-benzyl L-seryl L-valyl glycyl glycine methyl ester trifluoroacetate (34) (SEQ ID NO: 7)

N-tert-butoxycarbonyl O-benzyl L-seryl L-valyl L-valyl glycyl glycine methyl ester 24 (SEQ ID NO: 7) (0.525 g, 0.844 mmol) was dissolved in a 50% (v/v) solution of TFA in CH$_2$Cl$_2$ (12 mL) at room temperature. The reaction mixture was stirred for 1 h 30 min before the solvent and bulk of excess TFA were evaporated. Et$_2$O (10 mL) was added to the liquid residue, which resulted in precipitation of a white solid. The Et$_2$O was decanted off and the residue washed with additional portions of Et$_2$O (2×10 mL) and dried under reduced pressure overnight affording the title compound as a white solid (0.494 g, 92%); $\delta_H$ (300 MHz; d$_6$-DMSO) 8.47 (1H, d, J 9, NH(Val$_x$)), 8.29-8.20 (5H, m, NH$_3^+$/NH(Gly$_x$)/NH(Gly$_y$)), 8.00 (1H, d, J 8, NH(Val$_y$)) 7.38-7.27 (5H, m, Ph), 4.51 (2H, s, CH$_2$Ph), 4.34 (1H, dd, J 7 and 9, C$^\alpha$H(Val$_x$)), 4.17-4.12 (2H, m, C$^\alpha$H(Val$_y$)/C$^\alpha$H(Ser(Bn))), 3.85 (2H, dd, J 4 and 6, C$^\alpha$H$_2$(Gly$_x$)), 3.76-3.64 (4H, m, CH$_2$(Ser(Bn))/C$^\alpha$H$_2$(Gly$_y$)), 3.62 (3H, s, OCH$_3$), 2.04-1.89 (2H, m, CH(CH$_3$)$_2$), 0.89-0.81 (12H, m, CH$_3$); $\delta_C$ (75 MHz; d$_6$-DMSO) 171.1, 170.6, 170.1, 169.2, 166.2, 158.3 (q, J$_{CF}$ 32) 137.5, 128.2, 127.6, 127.5, 116.9 (q, J$_{CF}$ 291), 72.5, 68.6, 58.1, 57.9, 52.2, 51.6, 41.6, 40.5, 30.6, 30.2, 19.1, 19.1, 18.2, 18.0; m/z (ESI) 522.2920 (M$^+$; C$_{25}$H$_{40}$N$_5$O$_7$ requires 522.2927)

EXAMPLE 33

(S)-tert-butyl 2-((S)-2-(3S,6S,9S,12S)-6,9-diisopropyl-3-(2-methoxy-2-oxoethylcarbamoyl)-5,8,11-trioxo-1,14-dioxa-4,7,10-triazacyclooctadecan-12-ylcarbamoyl)pyrrolidine-1-carbonyl)pyrrolidine-1-carboxylate (35)

Palladium on activated carbon (10% (w/w) dry basis, wet (50% (w/w) H$_2$O)) (0.066 g, 0.0310 mmol Pd) was added carefully. Methanol (3 mL) was added. The reaction bottle was purged with hydrogen and a hydrogen balloon mounted on it. The reaction was stirred under hydrogen atmosphere at room temperature for 15 h 30 min. The balloon was removed and the reaction mixture, without prior concentration, applied on a silica column. The reaction mixture was purified by flash column chromatography (eluent: CH$_2$Cl$_2$/MeOH (16:1)). The solvents were evaporated and CH$_2$Cl$_2$ added. The solvent was evaporated affording a white solid (0.232 g). The crude product was further purified by preparative reversed phase HPLC (Analytical system: Agilent 1100 with DAD and MS/MS (3D Iontrap); Column: Supelco, Ascentis Express C18, 100 mm×4.6 mm ID, 2.7 μm; Temperature: 40° C.; Mobile phase: isocratic elution, 45% H$_2$O in MeOH; Flow: 1 mL/min; DAD: 205 nm; Injection volume: 5 μL). The solvents were evaporated affording a white solid (0.123 g, 49%); $\delta_H$ (300 MHz; CD$_2$Cl$_2$) 8.20 (1H, d, J 6, NH), 7.84 (1H, d, J 7, NH), 7.81-7.69 (2H, m, NH(Gly)/NH), 7.09 (1H, d, J 9, NH), 4.87-4.74 (1H, m, C$^\alpha$H), 4.56-4.44 (1H, ln, C$^\alpha$H), 4.44-4.36 (1H, m, C$^\alpha$H), 4.36-4.27 (1H, m, C$^\alpha$H), 4.27-4.14 (1H, m, C$^\alpha$H), 4.09-3.81 (6H, m, C$^\alpha$H/C$^\alpha$H/C$^\alpha$H/CH$_2$(Ser)/CHH(Ser)), 3.68 (3H, s, OCH$_3$), 3.76-3.53 (5H, m, CHH(Ser)/C$^\delta$H$_2$(Pro)/OCHHCH$_2$CH$_2$CHHO), 3.52-3.41 (2H, m, OCHHCH$_2$CH$_2$CHHO), 3.41-3.26 (2H, m, C$^\delta$H$_2$(Pro)), 2.48-1.40 (14H, m, CH$_2$(Pro)/CH(CH$_3$)$_2$/OCH$_2$CH$_2$CH$_2$CH$_2$O), 1.47 (9H, s, (CH$_3$)$_3$), 1.14-0.86 (12H,

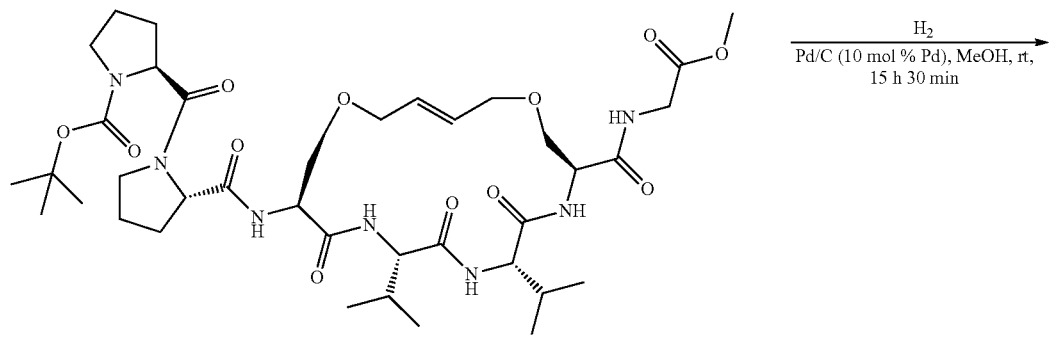

29

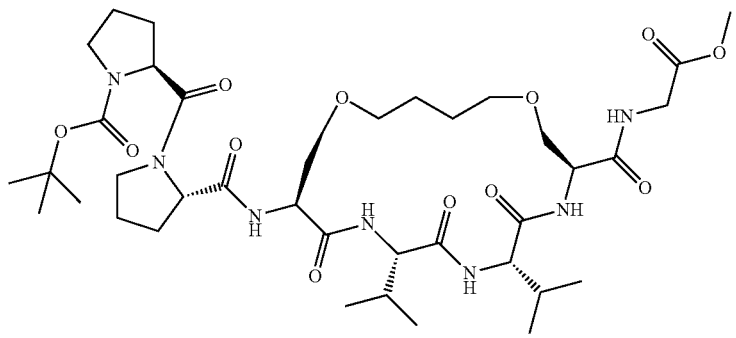

35

(S)-tert-butyl 2-((R)-2-((3S,6S,9S,12S,E)-6,9-diisopropyl-3-(2-methoxy-2-oxoethylcarbamoyl)-5,8,11-trioxo-1,14-dioxa-4,7,10-triazacyclooctadec-16-en-12-ylcarbamoyl)pyrrolidine-1-carbonyl)pyrrolidine-1-carboxylate (29) (0.249 g, 0.308 mmol) was dissolved in MeOH (15 mL).

m, CH$_3$); $\delta_H$ (75 MHz; CD$_2$Cl$_2$) 174.7, 172.9, 172.6, 172.5, 171.8, 171.3, 170.5, 155.5, 81.7, 73.2, 71.9, 70.4, 68.6, 63.6, 63.3, 63.0, 60.9, 56.6, 55.4, 52.3, 47.7, 47.3, 42.0, 30.8, 29.6, 29.3, 29.2, 28.5, 28.0, 26.7, 25.3, 25.0, 19.9, 19.8, 19.5, 19.5; m/z (ESI–) 808.45 ([M-H]$^-$; C$_{38}$H$_{62}$N$_7$O$_{12}$ requires 808.45)

In Vitro Function Studies
Compounds

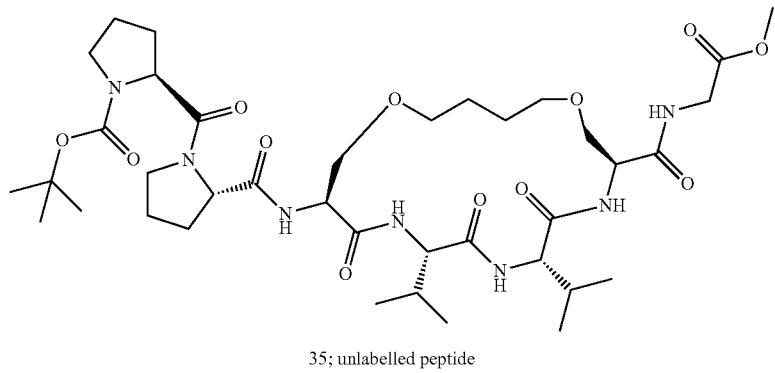

35; unlabelled peptide

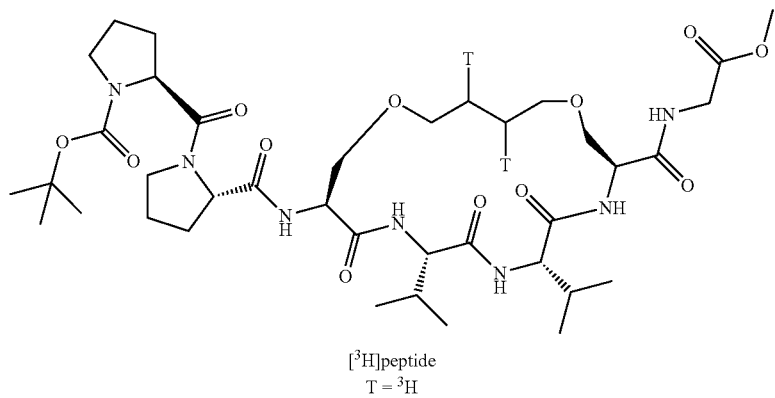

[³H]peptide
T = ³H

The radiolabelled compound denoted [3H]peptide was custom synthesised from the unsaturated precursor 29 (Example 27) by Perkin Elmer Health Sciences Inc., 549 Albany Street, Boston, Mass. 02118, U.S.A. The radioactive compound was received as an EtOH solution. The total activity of the sample was 1 mCi. and the radiological concentration was 2 mCi/mL. The specific activity was 42.9 Ci/mmol and the radiochemical purity (determined by HPLC) 99.8%. The specific activity was determined by mass spectrometry.

Animals

Female Wistar rats weighing 250-300 g (Mollegaard, Ejby, Denmark) were used. Experimental protocols conform to National Institutes of Health guidelines for the care and use of animals.

Tissue Preparation

Brain cerebella (1:5 wt/vol) in ice cold 0.3 M sucrose, 50 mM Hepes, pH 7.4, 2 mM EDTA, protease inhibitors (Complete; Roche, Mannheim, Germany) were homogenised in clay-beads-containing tubes by Fastprep shaker and centrifuged at 1,000 g for 10 min at 4° C. The supernatant was spun down at 42,000 g for 60 min at 4° C. The cytosolic protein containing supernatant was discarded, whereas the pellet containing the crude membranes was resuspended in ice cold 50 mM Hepes, pH 7.4, 2 mM EDTA. Protein concentration was determined by the DC Protein Assay Kit (Bio-Rad).

Radioligand Binding Assay

Binding assays were performed in 96-well, round-bottom microtiter plates with total reaction volume of 100 µl/well, containing the indicated concentration of [³H]peptide with or without competing unlabelled peptide (100 µM) in a binding buffer containing 50 mM Tris-HCl (pH 7.5 at RT), 1 mM EDTA, 5 mM EGTA, 2 mM MgCl$_2$, 1 mM ascorbate. The plates were incubated at 23EC for 60 min and harvested onto Multiscreen Harvest plate FC (Millipore, Ireland), presoaked in 0.3% polyethyleneimine (Sigma), using a Packard Filter-Mate Universal Harvester with 96-well format, and washed as quickly as possible 4 times with approx. 0.25 ml/well of ice-cold buffer, containing 50 mM Tris-HCl (pH 7.0 at RT) and 2 mM MgCl$_2$. The filters were dried and counted at approx. 40% efficiency in a Top-Count liquid scintillation counter (Packard) using 20 µl per filter well of Micro-Scint liquid scintillation cocktail (Packard).

Analysis of Binding Data

Binding data were analysed by non-linear regression using Microsoft Excel with the Solver add-in. The non-specific binding was assumed to be linear as a function of the concentration of free [³H]peptide and analysed by linear regression.

The total binding was modelled as the sum of the non-specific binding and the specific binding, defined by the equation:

$$Y = B_{max} * x/(K_d + x)$$

where $B_{max}$ is the total number of specific binding sites, $K_d$ the equilibrium dissociation constant and x the concentration of free [$^3$H]peptide.

Results—Compound 29 (of Example 27)

Specific binding of [$^3$H]peptide, defined as the difference in binding of [$^3$H]peptide in the absence and presence of 100 µM unlabelled peptide, i.e. specific binding=total binding (binding in the absence of unlabelled peptide)−non-specific binding (binding in the presence of unlabelled peptide), was detected in crude membranes from rat cerebellum, amounting to approx. 0.5-1 pmol/mg membrane protein and with a $K_d$ value (affinity) of about 0.1-0.2 µM.

| Results: | Un-weighted | Weighted 1/Y | Weighted 1/Y$^2$ |
|---|---|---|---|
| Kd (nM): | 106,568 | 92,679 | 92,679 |
| Bmax (fmol/mg protein): | 1120 | 1005 | 1005 |
| Bmax (cpm): | 2136.5 | 1918.3 | 1918.3 |

These results are presented in FIG. 1.

---

The invention claimed is:

1. A peptide comprising a unit of formula (II)

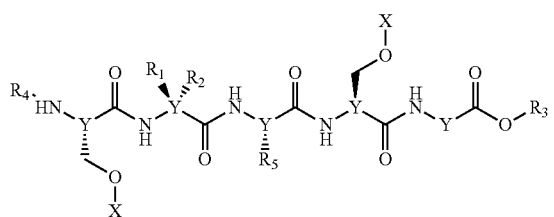

(II)

wherein each X is independently a $C_{1-6}$ alkyl or $C_{2-6}$ alkenyl group, or the two X groups taken together form a covalent or non-covalent link between the two O groups, which is a $C_{1-10}$ saturated or unsaturated carbon chain optionally interrupted by one or more heteroatoms selected from O, S, N, P, or Si, or one X represents an azido group and the other an $C_{2-6}$-alkynyl group;

each Y is independently C, CH, $CH_2$, N or NH;

$R_1$ is H or $C_{1-6}$ alkyl;

$R_2$ is H or $C_{1-6}$ alkyl;

$R_5$ is a $C_{1-6}$ alkyl group;

$R_3$ and $R_4$ are protective groups for carboxylic groups or amino groups respectively, fluorescent probes, radiolabeled groups or a further peptide chain with 1-20 amino acids in the chain, the end groups of which optionally carry protective groups for carboxylic groups or amino groups respectively, fluorescent probes, or radiolabeled groups;

or a salt of the peptide.

2. The peptide as claimed in claim 1 of formula A:

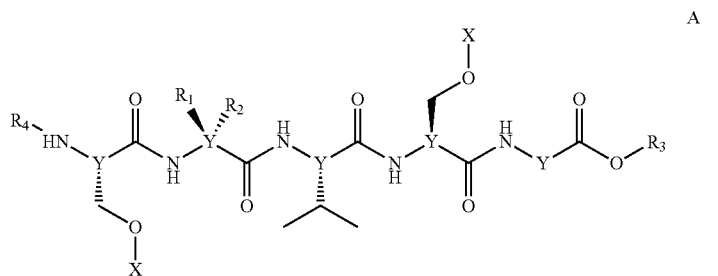

wherein each X is independently a $C_{1-6}$ alkyl or $C_{2-6}$ alkenyl group, or wherein the two X groups taken together form a covalent or non-covalent link between the two O groups, which is a $C_{1-10}$ saturated or unsaturated carbon chain optionally interrupted by one or more heteroatoms selected from O, S, N, P, or Si;

each Y is independently C or N, optionally comprising hydrogen to satisfy the valency of the atom;

each $R_1$ is independently $C_{1-6}$ alkyl or hydrogen;

each $R_2$ is independently $C_{1-6}$ alkyl or hydrogen; and $R_3$ and $R_4$ are protective groups for carboxylic groups or amino groups respectively, fluorescent probes, radiolabeled groups or peptide chains with 1-20 amino acids in the chain.

3. The peptide as claimed in claim 1, wherein the two X groups taken together form a saturated or unsaturated C3-10 carbon chain between the two O atoms.

4. The peptide as claimed in claim 1, wherein all Y groups are C.

5. The peptide as claimed in claim 1, wherein $R_1$ is isopropyl and $R_2$ is H, or $R_1$ is H and $R_2$ is isopropyl, or $R_1=R_2=$methyl.

6. The peptide as claimed in claim 1, wherein $R_3$ is a C-terminus peptide protecting group.

7. The peptide as claimed in claim 1, wherein $R_4$ is a N-terminus peptide protecting group.

8. The peptide as claimed in claim 1, wherein $R_4$ represents an addition amino acid chain of 1 to 5 units terminated by a peptide protecting group.

9. The peptide as claimed in claim 8, wherein said chain is $R_4$-Pro-Pro and $R_4$ is a protecting group.

10. The peptide as claimed in claim 1 of one of the following:

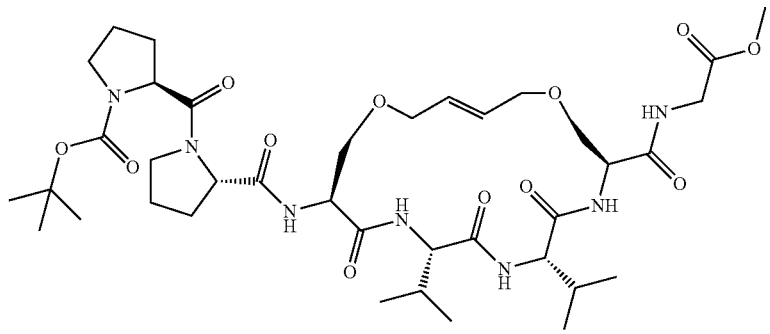

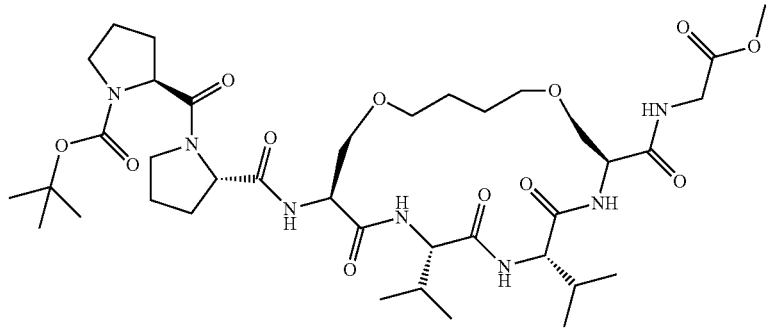

-continued

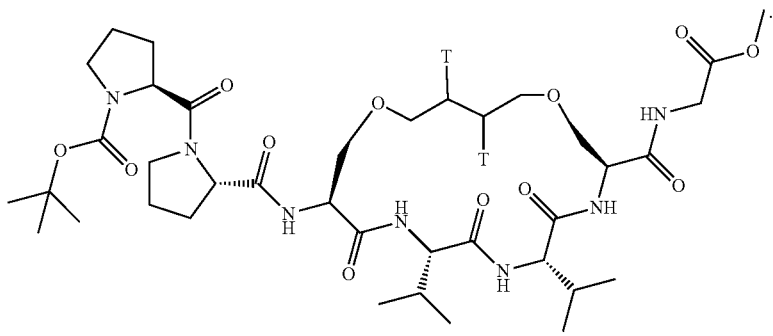

T = ³H

11. A pharmaceutical composition comprising a peptide as claimed in claim 1 along with at least one pharmaceutically acceptable excipient.

12. The peptide as claimed in claim 1, wherein each X is —CH$_2$—CH=CH$_2$.

13. The peptide as claimed in claim 1, wherein R$_5$ is isopropyl.

14. The peptide as claimed in claim 1, wherein R$_4$ is butyloxycarbonyl (Boc).

15. The peptide as claimed in claim 1, wherein the two X groups taken together form —CH$_2$CH=CHCH$_2$— or —CH$_2$CH$_2$CH$_2$CH$_2$—.

16. The peptide as claimed in claim 1, wherein R$_3$ is a methyl ester.

* * * * *

SEQUENCE LISTING

<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      backbone peptide

<400> SEQUENCE: 1

Ser Val Val Ser Gly
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      backbone peptide

<400> SEQUENCE: 2

Pro Pro Ser Val Val Ser Gly
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      backbone peptide

<400> SEQUENCE: 3

Asp Ser Ser Gly Glu Val Leu Ser Ser Val
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      backbone peptide

<400> SEQUENCE: 4

Asp Ser Ser Gly Glu
1               5

```
-continued

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      backbone peptide

<400> SEQUENCE: 5

Pro Pro Ser Val Val
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      backbone peptide

<400> SEQUENCE: 6

Ser Gly Val Ser Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      backbone peptide

<400> SEQUENCE: 7

Ser Val Val Gly Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      backbone peptide

<400> SEQUENCE: 8

Pro Pro Ser Val Val Gly Gly
1               5
```